United States Patent
Arnold et al.

(10) Patent No.: US 6,521,605 B1
(45) Date of Patent: Feb. 18, 2003

(54) AMIDOPHOSPHATE DERIVATIVES

(75) Inventors: Macklin Brian Arnold, Morgantown, IN (US); Paul Leslie Ornstein, Carmel, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/744,411

(22) PCT Filed: Jul. 28, 1999

(86) PCT No.: PCT/US99/17141

§ 371 (c)(1),
(2), (4) Date: Jan. 23, 2001

(87) PCT Pub. No.: WO00/06176

PCT Pub. Date: Feb. 10, 2000

Related U.S. Application Data

(60) Provisional application No. 60/094,904, filed on Jul. 31, 1998.

(51) Int. Cl.[7] .................... A61K 31/66; C07F 9/24; C07F 9/6553
(52) U.S. Cl. ................... 514/95; 514/137; 549/6; 558/199
(58) Field of Search .................... 549/6; 558/199; 514/95, 137

(56) References Cited

U.S. PATENT DOCUMENTS

| 4,132,702 A | 1/1979 | Schmidt et al. |
| 4,493,931 A | 1/1985 | Chekroun et al. |
| 6,174,922 B1 | 1/2001 | Arnold et al. |

FOREIGN PATENT DOCUMENTS

| WO | WO 98/33496 | 2/1997 |

OTHER PUBLICATIONS

Database CAPLUS on STN, Chemical Abstracts Service, (Columbus, Ohio), No. 1974:434602; Mukai et al., JP 48–033374 B4, Oct. 13, 1973.

Database CAPLUS on STN, Chemical Abstracts Service, (Columbus, Ohio), No. 1967:115610, Dregval et al., SU 184860, Jul. 30, 1966.

*Primary Examiner*—Robert Gerstl
(74) *Attorney, Agent, or Firm*—Nelsen L. Lentz

(57) ABSTRACT

The present invention provides amidophosphate derivatives useful for potentiating glutamate receptor function in a mammal and therefore, useful for treating a wide variety of conditions, such as psychiatric and neurological disorders.

12 Claims, No Drawings

AMIDOPHOSPHATE DERIVATIVES

This is a 371 of PCT/US99/17141 filed Jul. 28, 1999 which claims priority to U.S. Provisional Application No. 60/094,904, file Jul. 31, 1998.

The present invention relates to the potentiation of glutamate receptor function using certain amidophosphate derivatives. It also relates to novel amidophosphate derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.,* 21, 165 (1981); Monaghan, Bridges, and Cotman, *Ann. Rev. Pharmacol. Toxicol.,* 29, 365 (1989); Watkins, Krogsgaard-Larsen, and Honore, *Trans. Pharm. Sci.,* 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.,* 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.,* 11, 508 (1990); McDonald and Johnson, *Brain Research Reviews,* 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience,* September 1993, 13(9): 3904–3915 and Kathryn M. Partin, *J. Neuroscience,* Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron.* Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.,* Vol. 91, pp 777–781, 1994, *Neurobiology,* and Arai et al., *The Journal of Pharmacology and Experimental Therapeutics,* 278: 627–638, 1996.

It has now been found that cyclothiazide and certain amidophosphate derivatives potentiate agonist-induced excitability of human GluR4B receptor expressed in HEK 293 cells. Since cyclothiazide is known to potentiate glutamate receptor function in vivo, it is believed that this finding portends that the amidophosphate derivatives will also potentiate glutamate receptor function in vivo, and hence that the compounds will exhibit ampakine-like behavior.

The present invention provides compounds of formula I:

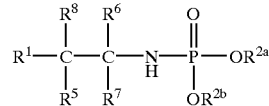

formula I wherein $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C) alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C)alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl,di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

The present invention further provides a method of potentiating glutamate receptor function in a mammal requiring such treatment, which comprises administering an effective amount of a compound of formula I.

According to another aspect, the present invention provides the use of a compound of formula I or a pharmaceutically acceptable salt thereof as defined hereinabove for the manufacture of a medicament for potentiating glutamate receptor function.

In addition, the present invention provides the use of a compound of formula I or a pharmaceutically acceptable salt thereof for potentiating glutamate receptor function.

The invention further provides a method of potentiating glutamate receptor function in a mammal requiring such treatment, which comprises administering an effective amount of a compound of formula:

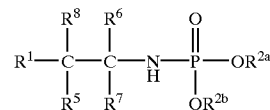

wherein $R^1$ represents an unsubstituted or substituted aromatic or heteroaromatic group; $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Huntington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as naphthyl.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

Examples of substituents which may be present in a substituted aromatic or heteroaromatic group include halogen; nitro; cyano; hydroxyimino; (1–10C) alkyl; (2–10C) alkenyl; (2–10C)alkynyl; (3–8C)cycloalkyl; hydroxy(3–8C) cycloalkyl; oxo(3–8C)cycloalkyl; halo(1–10C)alkyl; $(CH_2)_y X^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen;. nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, $OCONR^{19}$ or $NR^{19}COO$, $R^{15}$ represents hydrogen, (1–10C) alkyl, phenyl(1–4C)alkyl, halo(1–10)alkyl, (1–4C) alkoxycarbonyl(1–4C)alkyl, (1–4C)alkylsulfonylamino (1–4C)alkyl, N-(1–4C)alkoxycarbonyl)(1–4C) alkylsulfonylamino(1–4C)alkyl, (3–10C)alkenyl, (3–10C) alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (2–8C)alkenyl, (2–6C)alkenyl and (2–4C)alkenyl. Particular values are vinyl and prop-2-enyl.

The term (2–10C)alkynyl includes (3–10C)alkynyl, (2–8C)alkynyl, (2–6C)alkynyl and (3–4C)alkynyl. A particular value is prop-2-ynyl.

The term (3–8C)cycloalkyl, includes monocyclic and polycyclic groups. Particular values are cyclopropyl, cyclobutyl, cyclopentyl, cyclohexyl and bicyclo[2.2.2] octane. The term includes (3–6C)cycloalkyl: cyclopropyl, cyclobutyl, cyclopentyl and cyclohexyl.

The term hydroxy(3–8C)cycloalkyl includes hydroxy-cyclopentyl, such as 3-hydroxycyclopentyl.

The term oxo(3–8C)cycloalkyl includes oxocyclopentyl, such as 3-oxocyclopentyl.

The term halogen includes fluorine, chlorine, bromine and iodine.

The term halo(1–10C)alkyl includes fluoro(1–6C)alkyl, such as trifluoromethyl and 2,2,2-trifluoroethyl, and chloro (1–6C)alkyl, such as chloromethyl.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4] triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl4,5-dihydrothiazol-2-yl.

Preferably either one or two of $R^5$, $R^6$, $R^7$ and $R^8$ represents (1–6C)alkyl, aryl(1–6C)alkyl, (2–6C)alkenyl, aryl(2–4C)alkenyl or aryl, or two of $R^5$, $R^6$, $R^7$ and $R^8$ together with the carbon atom or carbon atoms to which they are attached form a (3–8C)carbocyclic ring; and the remainder of $R^5$, $R^6$, $R^7$ and $R^8$ represent hydrogen.

Examples of a (1–6C)alkyl group represented by $R^5$, $R^6$, $R^7$ and $R^8$ are methyl, ethyl and propyl. An example of an aryl(1-C)alkyl group is benzyl. An example of a (2–6C) alkenyl group is prop-2-enyl. An example of a (3–8C) carbocyclic ring is a cyclopropyl ring.

More preferably $R^6$ and $R^7$ represent hydrogen.

Preferably $R^5$ and $R^8$ each independently represents hydrogen or (1–4C)alkyl, or together with the carbon atom to which they are attached form a (3–8C) carbocyclic ring.

More preferably $R^8$ represents methyl or ethyl, or $R^5$ and $R^8$ together with the carbon atom to which they are attached form a cyclopropyl ring. When $R^8$ represents methyl or ethyl, $R^5$ preferably represents hydrogen or methyl.

Especially preferred are compounds in which $R^8$ represents methyl and $R^5$, $R^6$ and $R^7$ represent hydrogen.

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

$X^1$ preferably represents O, CO, CONH or NHCO.

z is preferably 0.

$R^9$ is preferably (1–4C)alkyl; (2–4C)alkenyl, (3–6C)cycloalkyl, pyrrolidinyl, morpholino or tetrahydrofuryl.

Particular values for the groups $(CH_2)_y X^1 R^9$ and $(CH_2)_z X^3 R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0, 1, 2 and 3.

$L^a$ and $L^b$ preferably each independently represents $CH_2$.

$X^2$ preferably represents a bond, O, NH, CO, CH(OH), CONH, NHCONH or $OCH_2CONH$.

Preferably the group $(CH_2)_y X^1 R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; $NHCOCOOCH3$; or 2-tetrahydrofurylmethoxy.

Preferably the group $(CH_2)_z X^3 R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_2$; CHO; $COCH_3$; COOH; $COOCH_3$; $CH_2NHCOOC(CH_3)_3$; $(CH_2)_2NHCOOC(CH_3)_3$; $NHSO_2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2N(OCOC(CH_3)_2SO_2CH_3$; $COCH_2NHSO_2CH_3$; $(CH_2)_2NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH=CH, CH=CHCN, $OCH_3$ or $O(CH_2)_3CH_3$.

Examples of particular values for $(L^a)_n—X^2—(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$.

$R^{14}$ is preferably an unsubstituted or substituted phenyl, naphthyl, furyl, thienyl, is oxazolyl, thiazolyl, tetrazolyl, pyridyl, pyrimidyl benzothienyl or benzothiazolyl group.

Examples of particular values for $R^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,4-dichlorophenyl, 3,5-dichlorophenyl, 4-cyanophenyl, 3-nitrophenyl, 4-hydroxyiminophenyl, 2-methylphenyl; 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, (1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxycarboxamido)ethylphenyl, 4-(2-t-butoxycarboxamido)ethylphenyl, 4-isopropylsulfonylaminophenyl, 4-(2-methanesulfonylamino)ethylphenyl, 4-(2-ethylsulfonylamino)ethylphenyl, 4-(3-isopropylsulfonylamino)propylphenyl, 4-(1-(2-(2-propane)sulfonylamino)propyl)phenyl, 4-(2-propylsulfonyl-amino)ethylphenyl, 4-(2-isopropylsulfonylamino)ethylphenyl, 4-(2-butylsulfonylamino)ethylphenyl, 4-(1-isopropylsulfonylaminomethyl)ethylphenyl, 4-(1-hydroxy-2-methane-sulfonylamino)ethylphenyl, 4-(2-(2,2,2-trifluoroethyl)-sulfonylaminoethyl)phenyl, 4-(2-cyclohexylsulfonylamino)-ethylphenyl, 4-(2-(2,2,2-trifluoroethyl)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl)sulfonylaminoethyl)phenyl, 4-(2-(4-fluoro-phenyl)sulfonylaminoethyl)phenyl, 4-(2-(2-trifluoromethyl-phenyl)sulfonylaminoethyl)phenyl, 4-(2-(4-trifluoro-methylphenyl)sulfonylaminoethyl)phenyl, 4-(2-(4-methoxyphenyl)sulfonylaminoethyl)phenyl, 4-(2-(1-(5-dimethylamino)napthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxycarbonyl)methanesulfonylaminoethanoyl)phenyl, 4-(2-(2-thienylcarboxamido)ethyl)phenyl, thien-2-yl, 5-hydroxymethylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol-4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydryl-imidazol-1-yl, [1,2,4]triazol-1-yl, tetrazol-5-yl, 2-methyltetrazol-5-yl, 2-ethyltetrazol-5-yl, 2-isopropyltetrazol-5-yl, 2-(2-propenyl)tetrazol-5-yl, 2-benzyl-tetrazol- 5-yl, pyrid-2-yl, 5-ethoxycarbonylpyrid-2-yl, pyrid-3-yl, 6-chloropyrid-3-yl, pyrid-4-yl, 5-trifluoro-methylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl).

More preferably, $R^1$ represents 2-naphthyl or a group of formula

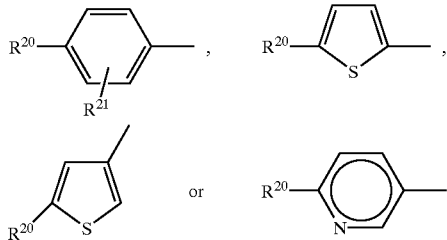

in which $R^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; $(CH_2)_yX^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}{}_1$, $R^9$ represents hydrogen, (1–10C) alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl-dihydrothiazolyl; (1–4C) alkoxycarbonyldimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}—(L^a)_n—X^2—(L^b)_m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C) alkylene, one of n and m is 0 or 1 and the other is 0, and $R^{14}$ represents a phenyl or hetero-aromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl): halo(1–10C)alkyl; cyano(2–10C)alkenyl; phenyl; $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10)alkyl, (1–4C)alkoxycarbonyl(1–4C)alkyl, (1–4C)alkylsulfonylamino(1–4C)alkyl (N-(1–4C)alkoxycarbonyl)(1–4C)alkylsulfonylamino(1–4C)alkyl, (3–10C)alkenyl, (3–10C)alkynyl, (3–8C) cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamido, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro-4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetyl-phenyl, 4-acetylphenyl, 4-carboxyphenyl, 2-methoxyphenyl, 4-methoxyphenyl, 2-hydroxymethylphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxyaminoethyl)phenyl, 4-(2-t-butoxycarboxyaminoethyl)phenyl, benzylsulfonylamino, 4-isopropylsulfonylaminophenyl, 4-(2-methanesulfonyl-aminoethyl)phenyl, 4-(2-ethylsulfonylaminoethyl)phenyl, 4-(2-propylsulfonylaminoethyl)phenyl, 4-(2-butylsulfonyl-aminoethyl)phenyl, 4-(2-isopropylsulfonylaminoethyl) phenyl, 4-(1-hydroxy-2-methanesulfonylaminoethyl) phenyl, 4-(2-dimethylaminosulfonylaminoethyl)phenyl, 4-(1-(2-(2-propyl)sulfonylaminopropyl)phenyl, 4-(2-(2,2,2-trifluoro-ethyl)sulfonylaminoethyl)phenyl, 4-(2-cyclohexylsulfonyl-aminoethyl)phenyl, 4-(2-phenylsulfonylaminoethyl)phenyl, 4-(2-(2-fluorophenyl) sulfonylaminoethyl)phenyl, 4-(2-(4-fluorophenyl) sulfonylaminoethyl)phenyl, 4-(2-(2-trifluoromethylphenyl) sulfonylaminoethyl)phenyl, 4-(2-(4-trifluoromethylphenyl) sulfonylaminoethyl)phenyl, 4-(2-(4-methoxyphenyl) sulfonylaminoethyl)phenyl, 4-(2-(1-(5-dimethylamino) napthalenesulfonylamino)ethyl)phenyl, 4-(2-(2-thienyl) sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2- methoxybenzamido)ethyl)phenyl, 4-(2-(2-thienyl-carboxamido)ethyl)phenyl, 4-carbamoylphenyl, 4-methylcarbamoylphenyl, 4-dimethylcarbamoylphenyl, 4-(2-(2-methylpropaneamido)ethyl)phenyl, 4-(2-(3-methylbutaneamido)ethyl)phenyl, benzoylmethyl, benzamido, 2-fluorobenzamido, 3-flurobenzamido, 4-fluorobenzamido, 2,4-difluorobenzamido, 3chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethyl-benzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluoro-benzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methylisoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)-carboxamido, 2-pyridylcarboxamido, 6-chloro-2-pyridyl-carboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl)-phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)-phenyl, 4-(4-formylphenyl)phenyl, 4-(4-methylphenyl)phenyl and 4-(2-methoxyphenyl)phenyl.

The compounds of formula I can be prepared as described in Scheme I. The reagents and starting materials are readily available to one of ordinary skill in the art. All the substituents, unless otherwise specified, are previously defined.

Scheme I

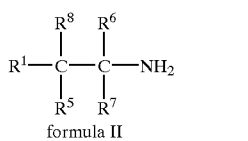

formula II

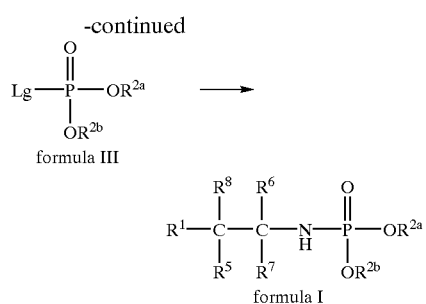

In Scheme I, the compound of formula II is reacted with the compound of formula III under standard conditions well known in the art, to provide the compound of formula I. More specifically, the compound of formula II is dissolved in a suitable organic solvent. Examples of suitable organic solvents include methylene chloride, tetrahydrofuran, acetonitrile, and the like. The solution is treated with a slight excess of a suitable base, and then cooled to about −78° C. to about 0° C. Examples of suitable bases include triethylamine, pyridine, potassium carbonate, and the like. To the stirring solution is added one equivalent of a compound of formula II. The term "Lg" as used herein refers to a suitable leaving group. Examples of suitable leaving groups include, Cl, Br, I, and the like. Cl is the preferred leaving group. The reaction mixture is stirred at about −78° C. to about 50° C. for about 0.5 hours to about 16 hours. The compound of formula I is then isolated and purified by techniques well known in the art, such as extraction techniques and chromatography.

For example, the reaction is treated with a suitable acid, such as dilute hydrochloric acid, to neutralize or make the solution slightly acidic and then extracted a suitable organic solvent, such as methylene chloride. The organic extracts are combined, dried over anhydrous magnesium sulfate, filtered and concentrated under vacuum to provide the crude material of formula I. The crude material can. be purified by flash chromatography on silica gel with a suitable eluent to provide the purified compound of formula I. Examples of suitable eluents are ethyl acetate, ethyl acetate/hexane, and the like.

The compounds of formula I in which $R^1$ represents a 4-bromophenyl group may conveniently be converted into other compounds of formula I in which R represents another 4-substituted phenyl group by reaction with an appropriate boronic acid derivative, for example, a benzeneboronic acid derivative. The reaction is conveniently performed in the presence of a tetrakis (triarylphosphine)palladium(0) catalyst, such as tetrakis (triphenylphosphine)palladium(0) and a base such as potassium carbonate. Convenient solvents for the reaction include aromatic hydrocarbons, such as toluene. The temperature at which the reaction is conducted is conveniently in the range of from 0 to 150° C., preferably 75 to 120° C. Bis aromatic intermediates useful in the preparation of compounds of formula I may be prepared by reacting a bromoaromatic or bromoheteroaromatic compound with an aromatic or heteroaromatic boronic acid in an analogous manner.

More specifically, for example, to a degassed solution of a compound of formula I wherein $R^1$ represents a 4-bromophenyl group, approximately 1.5 equivalents of a benzeneboronic acid derivative, such as 3-fluorobenzeneboronic acid, and approximately 1.5 equivalents of potassium carbonate in a suitable organic solvent, such as toluene, is added a catalytic amount of bis(triphenylphosphine)palladium(II) dichloride. The mixture is heated to about 100° C. for about 16 hours, cooled to ambient temperature and diluted with ethyl acetate. The mixture is washed with water and the organic portion is separated. The aqueous portion is extracted with ethyl acetate and the combined organics are dried over anhydrous magnesium sulfate, filtered and concentrated under vacuum. Chromatography on silica gel with a suitable eluent, such as ethyl acetate/toluene provides the desired bis aromatic compound of formula I (See Table I, Example 4).

The boronic acid derivative used as a starting material may be prepared by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate.

Alternatively, the compounds of formula I in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine)-palladium(0) and hexaalkyldistannane, where the alkyl group is methyl or n-butyl, in an aprotic solvent such as toluene in the presence of a tertiary amine base such as triethylamine, at temperatures ranging from 80 to 140° C., preferably from 90 to 110° C.

The compounds of formula I in which $R^1$ represents a 4-(tri-n-butylstannyl)phenyl group may then be reacted with an aryl- or heteroarylbromide, such as 2-bromothiophene-5-carboxaldehyde, in the presence of a palladium(0) catalyst, such as tetrakis(triphenylphosphine)palladium(0), or a palladium(II) catalyst, such as bis(triphenylphosphine)-palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula I in which $R^1$ represents a 4-bromophenyl group may be converted into other compounds of formula I in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentyl-magnesium bromide, in the presence of a palladium(II) catalyst, such as [1,1'-bis(diphenylphosphino)ferrocene]-dichloropalladium(II) ($PdCl_2(dppf)$), in an aprotic solvent, such as diethyl ether at temperatures ranging from −78° C. to 25° C.

The compounds of formula I in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenyl-phosphine)palladium(II) dichloride and sodium formate in an aprotic solvent, such as dimethylformamide at temperatures ranging from 70 to 110° C., preferably at 90° C.

The compounds of formula I in which $R^1$ represents a 4-hydroxyphenyl group may be converted into other compounds of formula I in which $R^1$ represents an alkoxy group by treatment of the corresponding hydroxyphenyl group with an appropriate alkylhalide such as benzylbromide in the presence of sodium hydride in an aprotic solvent such as dimethylformamide at temperatures ranging from 25 to 100° C., preferably from 50 to 90° C.

The compounds of formula II are known or may be prepared by conventional methods, for example by reducing a corresponding amide or nitrile using borane.

Some of the nitriles or amides used as starting materials may conveniently be prepared by treatment of an acetonitrile of formula $R^1CH_2CN$, for example a substituted phenylacetonitrile such as 4-methoxyphenylacetonitrile or an acetate of formula $R^1CH_2COOR$ (where R is, for example alkyl), for example a phenylacetate such as methyl 4-tert-butylphenylacetate, with a strong lithium amide base, such as sodium or lithium bis(trimethylsilyl) amide, and an alkylhalide, such as methyl iodide, in an aprotic solvent, such as tetrahydrofuran, at a temperature ranging from −78 to 25° C. The esters are converted to amides by hydrolysis (water, alcohol and sodium or potassium hydroxide) to the acid, conversion of the acid to the acid chloride ($SOCl_2$ or $(COCl)_2$ plus DMF (1 drop)) then conversion to the amide with aqueous ammonia and a co-solvent such as tetrahydrofuran or dioxane.

Certain nitriles used to prepare compounds of formula II may also conveniently be prepared by reacting a corresponding ketone derivative, for example a compound of formula $R^1COR^8$, such as (2-acetyl-5-thien-3-yl)thiophene, with tosylmethylisocyanide and potassium t-butoxide in dimethyl ether or dimethoxyethane.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 $\mu$l of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 pM Fluo3-AM dye (obtained from Molecular Probes Inc., Eugene, Oreg.) in buffer in each well. After the incubation, each well is washed once with 100 $\mu$l buffer, 200 $\mu$l of buffer is added and the plates are incubated for 30 minutes.

Solutions for use in the test are also prepared as follows 30 $\mu$M, 10 $\mu$M, 3 $\mu$M and 1 $\mu$M dilutions of test compound are prepared using buffer from a 10 mM solution of test compound in DMSO. 100 $\mu$M cyclothiazide solution is prepared by adding 3 $\mu$l of 100 mM cyclothiazide to 3 ml of buffer. Control buffer solution is prepared by adding 1.5 $\mu$l DMSO to 498.5 $\mu$l of buffer.

Each test is then performed as follows. 200 $\mu$l of control buffer in each well is discarded and replaced with 45 $\mu$l of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 $\mu$l of buffer and 45 $\mu$l of test compound in buffer in appropriate wells. A second fluorescent reading is taken after 5 minutes incubation. 15 $\mu$l of 400 $\mu$M glutamate solution is then added to each well (final glutamate concentration 100 $\mu$M), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM, cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis (oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM, they produce a greater than is 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

FORMULATION 1
Hard gelatin capsules are prepared using the following ingredients:

| | Quantity (mg/capsule) |
|---|---|
| Active Ingredient | 250 |
| Starch, dried | 200 |
| Magnesium Stearate | 10 |
| Total | 460 |

The above ingredients are mixed and filled into hard gelatin capsules in 460 mg quantities.

FORMULATION 2
Tablets each containing 60 mg of active ingredient are made as follows:

| | Quantity (mg/tablet) |
|---|---|
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S sieve. The sodium carboxymethyl starch, magnesium stearate, and talc, previously passed through a No. 60 mesh U.S. sieve, are then added to the granules which, after mixing, are compressed on a tablet machine to yield tablets each weighing 1.50 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples represent typical syntheses of the compounds of formula I as described generally above. These examples are illustrative only and are not intended to limit the invention in any way. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "iPrOAc" refers to isopropyl acetate; "EtOAc" refers to ethyl acetate; "Me" refers to a methyl group: "Et" refers to an ethyl group: "iPr" refers to an isopropyl group; "Bu" refers to a butyl group; and "RT" refers to room temperature.

Preparation 1

2-(4-Bromophenyl)propionitrile

A solution of 50.0 g (225.0 mmol) of 4-bromophenylacetonitrile and 1.8 g (12.8 mmol) of potassium carbonate in 387 mL of dimethyl carbonate was heated to 180° C. in a sealed vessel for 16 hours. The solution was then cooled, diluted with 200 ml of ethyl acetate and washed once with 100 ml water, once with 100 ml of 10% aqueous sodium bisulfate and once with 100 ml brine. The organic portion was dried (MgSO$_4$), filtered and concentrated in vacuo. The residue was distilled under vacuum through a short path distillation apparatus to afford 40.3 g (85%) of the title compound.

Preparation 2

2-(4-Bromophenyl)propylamine hydrochloride

To a solution of 35.2 g (167.6 mmol) of material from Preparation I under reflux in 35.0 mL of tetrahydrofuran was added 18.4 ml (184.3 mmol) of 10M borane-dimethylsulfide slowly via a syringe. The solution was heated under reflux for an additional 1 hour after the addition was complete. The solution was cooled to ambient temperature and a saturated solution of hydrogen chloride in methanol was added slowly until pH 2 was achieved. The resulting slurry was concentrated in vacuo. The residue was dissolved in methanol and concentrated in vacuo twice. The resulting solid was suspended in ethyl ether, filtered, rinsed with ethyl ether and dried in vacuo to afford 31.2 g (74%) of the title compound.

Preparation 3

2-Fluorobenzeneboronic Acid

A solution of 50 g (285.6 mmol) of 2-fluorobromobenzene in 400 mL of tetrahydrofuran was cooled to −78° C. and 200 mL (320.0 mmol) of 1.6M n-Butyllithium was added via a cannula. The mixture was stirred at −78° C. for 60 minutes, then 98.9 mL (428.4 mmol) of triisopropyl borate was added via a cannula and stirring was continued for 60 minutes. The cooling bath was removed and the mixture was stirred at ambient temperature for 1.5 hours, then 150 mL of 6N hydrochloric acid was added and stirring was continued for 1.5 hours. To the mixture was added 100 mL of brine, and then the organic layer was separated and the aqueous layer was extracted three times with 30 mL each of ether. The combined organic extracts were dried (MgSO$_4$), filtered and concentrated in vacuo. The residue was recrystallized from water to afford 25.2 g (63%) of the title compound.

Preparation 4

2-(4-bromophenyl)-N-(t-butoxycarbonyl) propylamine

To a solution of 11.8 g (55.0 mmol) of material from Preparation 2 in 100 mL of chloroform and 100 mL of saturated sodium bicarbonate was added 12.0 g (55.0 mmol) of di-tert-butyl dicarbonate. The solution was stirred at ambient temperature for 1 hour. The organic layer was separated and the aqueous layer was extracted three times with 30 mL each of chloroform. The combined organic extracts were dried (MgSO$_4$), filtered and concentrated in vacuo to afford 16.5 g (95%) of the title compound.

Preparation 5

2-(4-(2-fluorophenyl)phenyl)-N-(t-butoxycarbonyl) propylamine

To a degassed solution of 12.5 g (39.8 mmol) of material from Preparation 4, 6.7 g (47.7 mmol) of material from Preparation 3 and 8.2 g (59.7 mmol) of potassium carbonate in 140 mL of toluene was added 2.3 g (1.9 mmol) of tetrakis (triphenylphosphine)palladium(0). The mixture was heated at 90° C. for 18 hours. The mixture was then cooled to ambient temperature and 300 mL of water and 150 mL of ether were added. The organic layer was separated and the aqueous layer was extracted three times with 50 mL each of ethyl acetate. The combined organic extracts were dried (MgSO$_4$), filtered and concentrated in vacuo. Chromatography (500 g of silica gel, 10% ethyl acetate/hexane) of the residue afforded 9.3 g (71%) of the title compound.

Preparation 6

2-(4-(2-fluorophenyl)phenyl)propylamine

A solution of 9.3 g of material from Preparation 5 in 100 mL 20% trifluoroacetic acid/dichloromethane was stirred at ambient temperature for 2 hours. The mixture was concentrated in vacuo to afford 11.7 g of material. The material was dissolved in 100 mL of ether and washed twice with 50 mL of 1N sodium hydroxide. The organic layer was concentrated in vacuo to afford 5.48 g (85%) of the title compound.

Preparation 7

2-(4-Isopropylphenyl)propionitrile

In a 250 ml flask, 4-isopropylphenylacetonitrile 8.00 g (50.2 mmol) was dissolved in tetrahydrofuran (150 ml) under a nitrogen atmosphere. The solution was cooled to −78° C. and lithium bis(trimethylsilyl)amide (1M in tetrahydrofuran, 52.8 ml (52.8 mmol) added. The resulting mixture was stirred at −78° C. for 1 hour. To this reaction mixture was added iodomethane 3.29 ml (52.8 mmol). The resulting mixture was slowly allowed to warm to ambient temperature over 16 hours then quenched with 0.2M hydrochloric acid and extracted twice with diethyl ether. The organic fractions were combined, dried (MgSO$_4$) and concentrated under vacuo. Chromatography (SiO$_2$, 20% ethyl acetate/hexanes) gave 6.32 g (73%) of the title compound.

Field Desorption Mass Spectrum: M=173.

Analysis for C$_{12}$H$_{15}$N: Theory: C, 83.19; H, 8.73; N, 8.08. Found: C, 82.93; H, 8.57, N, 8.02.

Preparation 8

2-(4-Isopropylphenyl)propylamine hydrochloride

In a 100 ml flask, fitted with a condenser, 2-(4-isopropylphenyl) propionitrile 1.90 g (11.0 mmol) was dissolved in tetrahydrofuran (70 ml) under a nitrogen atmosphere. Borane-methyl sulfide complex (10.0–10.2 M in tetrahydrofuran, 1.20 ml, 12.1 mmol) was added to the solution and the mixture heated to reflux for 3 hours. The solution was cooled to ambient temperature and a saturated solution of hydrochloric acid in methanol added slowly until a white precipitate formed. The solvent was removed in vacuo and the resulting white solid triturated (×4) with diethyl ether. Drying under vacuo gave 1.76 g (73%) of the title compound.

Preparation 9

2-(4-Methoxyphenyl)propionitrile

Following the method of Preparation 7, but using 4-methoxyphenylacetonitrile 5.00 g (34.0 mmol), 6.32 g of the title compound was obtained.

Field Desorption Mass Spectrum: M=161.

Analysis for C$_{10}$H$_{11}$NO: Theory: C, 74.51; H, 6.88; N, 8.69. Found: C, 74.34; H, 6.67; N, 8.93.

Preparation 10

2-(4-Methoxyphenyl)propylamine hydrochloride

Following the method of Preparation 8, but using the product of Preparation 9, 2.75 g (17.1 mmol), 2.77 g (81%) of the title compound was obtained.

Analysis for C$_{10}$H$_{16}$ClNO: Theory: C, 59.55; H, 8.00; N, 6.94. Found: C, 59.33; H 7.89; N, 6.71.

Preparation 11

Methyl 2-(4-t-butylphenyl)propanoate 23.3 mL of lithium bis(trimethylsilyl)amide (1.0 M, 23 mmols) was added dropwise to 4.75 g (23 mmols) of methyl 4-tert-butylphenylacetate in 100 mL of dry THF at −78° C. while stirring under nitrogen. The mixture was stirred at this temperature for 45 minutes, then 1.5 mL (24 mmol) methyl iodide was added dropwise and the solution was stirred for an additional 1 hour at −78° C. The mixture was poured into 200 mL of H$_2$O and the desired product was extracted with 500 mL diethyl ether. The organic layer was backwashed once with 500 mL H$_2$O, dried over K$_2$CO$_3$, and concentrated under reduced pressure to yield 5.12 g of a dark oil. The oil was purified via silica gel chromatography eluting with a solvent gradient of hexane to hexane/ethyl acetate 19:1. The fractions containing the desired product were combined and concentrated under reduced pressure to yield the title compound 2.65 g (53%).

Mass Spectrum: M=220.

Preparation 12

Methyl 2-(4-t-butylphenyl)butanoate 4 g (19 mmol) of methyl 4-tert-butylphenylacetate, 19.5 mL (1.0 M, 19 mmol) of lithium bis(trimethylsilyl)amide and 3.12 g (20 mmol) of ethyl iodide were reacted as described in Preparation 11 to yield 5.13 g of a brown oil. Chromatography, eluting with a gradient solvent of hexane to hexane/ethyl acetate 19:1 gave the title compound 2.35 g (53%).

Mass Spectrum: M=234.

Preparation 13

Methyl 2-(4-t-butylphenyl)-2-methylpropanoate 4.75 g (23 mmol) of methyl 4-tert-butylphenylacetate, 46.6 mL (1.0 M, 46 mmol) of lithium bis(trimethylsilyl)amide, and 6.80 g (48 mmols) of methyl iodide were reacted as described in Preparation 11 to yield 4.73 g of a crude oil.

Chromatography, eluting with a solvent gradient of hexane to hexane/ethyl acetate 19:1, gave the title compound 2.0 g (37%).

Mass Spectrum: M=234.

Preparation 14

Ethyl 2-(2-naphthyl)propanoate 5 g (23 mmol) of ethyl 2-naphthylacetate, 23.3 mL (1.0 M, 23 mmol) of lithium bis(trimethylsilyl)amide, and 1.5 mL (24 mmol) of methyl iodide were reacted as described in Preparation 11 to yield 5.71 g of a dark oil. Chromatography eluting with a solvent gradient of hexane to hexane/ethyl acetate 19:1 gave the title compound 2.85 g (54%).

Mass Spectrum: M=228.

Preparation 15

2-(4-t-butylphenyl)propanoic Acid 2.60 g (12 mmol) of the product of Preparation 11 and 1.75 g (42 mMol) of lithium hydroxide were placed into a tri-solvent solution of tetrahydrofuran (189 mL), CH$_3$OH (63 mL), and H$_2$O (63 mL) and stirred at ambient temperature for 16 hours. The mixture was then concentrated under reduced pressure and the resulting white solid was taken into 200 mL 1N HCl and the desired product was extracted with 250 mL ethyl acetate. The organic layer was concentrated under reduced pressure to give the title compound 1.21 g (49%).

Mass Spectrum: M=206.

Preparation 16

2-(4-t-butylphenyl)butanoic Acid

The title compound (2.14 g) was prepared by the method of Preparation 15, starting from the product of Preparation 12, and recrystallized from hexane.

Mass Spectrum: M=220.

Preparation 17

2-(4-t-butylphenyl)-2-methylpropanoic Acid

The title compound (1.75 9) was prepared by the method of Preparation 15 starting from the product of Preparation 13, and recrystallized from hexane.

Mass Spectrum: M=220.

Preparation 18

2-(2-Naphthyl)propanoic Acid

The title compound (3.81 g) was prepared by the method of Preparation 15 starting from the product of Preparation 14, and recrystallized from hexane/ethyl acetate 9:1.

Mass Spectrum: M=214.

Preparation 19

2-(4-t-butylphenyl)propionamide 900 mg (4.4 mmol) of the product of Preparation 15 was added portionwise to oxalyl chloride (10 mL) at ambient temperature under $N_2$ followed by $CH_2Cl_2$ (10 mL). Initiation of the reaction was accomplished by the addition of one drop of DMF. An evolution of gas appeared and the reaction was stirred at ambient temperature for 2 hours. The solution was concentrated under reduced pressure to yield an oil. Dioxane (10 mL) was added for solubility and while stirring at ambient temperature, 28% ammonium hydroxide (10 mL) was added and the reaction was stirred for 16 hours. The solution was then concentrated under reduced pressure to yield a white solid. This solid was taken into 50 mL ethyl acetate, backwashed once with 50 mL $H_2O$, dried over $K_2CO_3$, and concentrated under reduced pressure to yield 770 mg of a solid. Recrystallization from hexane/ethyl acetate 1:1 gave the title compound 555 mg (61%).

Mass Spectrum: M=205.

Preparation 20

2-(4-t-butylphenyl)butanamide

The title compound was prepared by the method of Preparation 19, starting from the product of Preparation 16. Purification was achieved by silica gel chromatography (Chromatotron-2000 micron rotor) eluting with a solvent of hexane/ethyl acetate 1:1 to yield 471 mg (60%).

Mass Spectrum: M=219.

Preparation 21

2-(4-t-butylphenyl )-2-methylpropionamide

The title compound was prepared following the method of Preparation 19, starting from the product of Preparation 17. The crude product was triturated with a solution of hexane/ethyl acetate 19:1 for ½ hour and filtered to yield 1.16 g of a white solid. Subsequent recrystallization from ethyl acetate/ethanol 1:1 gave an 80% recovery as platelets.

Mass Spectrum: M=219.

Preparation 22

2-(2-Naphthyl)propionamide

The title compound was prepared following the method of Preparation 19, starting from the product of Preparation 18. Recrystallization from hexane/ethyl acetate 1:1 yielded 1.65 g (90%).

Mass Spectrum: M=199.

Preparation 23

2-(4-t-butylphenyl)propylamine 25 mL of Borane-tetrahydrofuran complex (1.0 M, 0.025 Mol) was added via a syringe to 1.10 g (5.4 mmol) of the product of Preparation 19 (60 mL) at ambient temperature under $N_2$. The mixture was then heated at 60–65° C. for 16 hours. A saturated HCl/methanol solution (5 mL) was then added via a syringe at ambient temperature with severe foaming and the solution was then concentrated under reduced pressure. The resulting white solid was taken into 100 mL 1 N NaOH and the liberated free amine was extracted once with 200 ml diethyl ether. The organic layer was backwashed once with 200 mL $H_2O$, dried over $K_2CO_3$, and concentrated under reduced pressure to yield 1.21 g of a brown oil. Chromatography (Chromatotron-2000 micron rotor) eluting with a gradient solvent of ethyl acetate/MeOH 9:1 to MeOH gave 856 mg (83%).

Mass Spectrum: M=191.

Preparation 24

2-(4-t-butylphenyl)butylamine

The title compound 540 mg was prepared as an oil by the method of Preparation 23, starting from the product of Preparation 20.

Mass Spectrum: M=205.

Preparation 25

2-(4-t-butylphenyl)-2-methylpropylamine

The title compound 428 mg (42%) was prepared following the method of Preparation 23, starting from the product of Preparation 21, and using methanol as the chromatography solvent.

Mass Spectrum: M=205.

Preparation 26

2-(2-Naphthyl)propylamine

The title compound, 450 mg (44%) was prepared as an oil following the method of Preparation 23, starting from the product of Preparation 22, and using methanol as the chromatography solvent.

Mass Spectrum: M=185.

Preparation 27

Methyl 1-(4-t-butylphenyl)cyclopropanecarboxylate 4 g (19.4 mmol) of Methyl 4-tert-butylphenylacetate, 39 mL (1.0 m, 2 Eq.) of lithium bis(trimethylsilyl)amide, and 3 g (2 Eq.) of 1-bromo-2-chloroethane in 100 mL dry THF were reacted as described in Preparation 11, except that the reaction mixture was stirred for one hour at ambient temperature before work-up. This reaction yielded 4.21 g of a brown oil. This material was purified via silica gel chromatography eluting with a gradient solvent of hexane to hexane/EtOAc 19:1 to yield the title compound 1.57 g (35%) as a pale yellow solid m.p. 58°–60° C. Calculated for $C_{15}H_{20}O_2$: Theory: C, 77.37; H, 8.81 Found: C, 77.54; H, 8.68.

Preparation 28

1-(4-t-butylphenyl)cyclopropanecarboxylic acid 1 g (4.3 mmol) of the product of Preparation 27 and 650 mg (15.5 mmol) of lithium hydroxide were placed in a tri-solvent solution of THF (66 mL), methanol (22 mL), and $H_2O$ (22 mL) and reacted as described in Preparation 15 to yield 840 mg of a solid. This material was purified via silica gel chromatography eluting with hexane/EtOAc 1:1 as a solvent to yield the title compound, 600 mg, (64%) as a white solid. m.p. dec>150° C. Calculated for $C_{14}H_{18}O_2$: Theory: C, 77.03; H, 8.31 Found: C, 77.08; H, 8.02.

Preparation 29

1-(4-t-butylphenyl)cyclopropanecarboxamide 580 mg. (2.7 mmol) of the product of Preparation 27, oxalyl chloride (10 mL), methylene chloride (10 mL) and one drop DMF were reacted as described in Preparation 19 to yield 573 mg of the crude acid chloride. Amide conversion was accomplished with 28% ammonium hydroxide (10 mL) and dioxane (10 mL) as described in Preparation 27 to yield 590 mg of a solid. Trituration in hexane/EtOAc. 19:1 and subsequent filtration yielded 510 mg (87%) of the title compound as a white solid. m.p. 178°–180° C. Calculated for $C_{14}H_{19}NO$: Theory: C, 77.38; H, 8.81; N, 6.45 Found: C, 77.53; H, 8.77; N, 6.39.

Preparation 30

1-(4-t-butylphenyl)cyclopropylmethylamine 7 mL of Borane-tetrahydrofuran complex (1.0 M, 7 mmol) and 500 mg (2.3 mmol) of the product of Preparation 29 in THF (50 mL) were reacted as described in Preparation 23 to yield 510 mg of an oil. Purification was achieved via silica gel chromatography eluting with a gradient solvent of EtOAc/methanol 9:1 to methanol to yield 222 mg (47%) as a solid, m.p. 39°–41° C. Calculated for $C_{14}H_{21}N$: Theory C, 82.70; H, 10.41; N, 6.89 Found: C, 81.36; H, 10.13; N, 7.24.

Preparation 31

2-(4-Bromophenyl)propylamine hydrochloride

To a –15° C. solution of 50.0 g (251.2 mmol) of 4-bromo-acetophenone and 49.0 g (251.2 mmol) of tosylmethyl iso-cyanide in 800 mL of dry dimethoxyethane was added a hot solution of 50.7 g (452.2 mmol) of potassium tert-butoxide in 230 mL of tert-butyl alcohol dropwise at a rate to maintain the temperature below 0° C. The reaction was stirred at –5° C. for 45 min after addition was complete. The cooling bath was removed and the reaction stirred for 2.5 h more. The mixture was concentrated in vacuo to a volume of 200 mL and diluted with 500 mL of water. The aqueous mixture was extracted four times with diethyl ether, and the combined organic portions were dried ($MgSO_4$), filtered and concentrated in vacuo. The residue was dissolved in 55 mL of tetrahydrofuran and heated to reflux. To the refluxing solution was added slowly dropwise 27.6 mL (276.3 mmol) of 10.0 M borane-dimethylsulfide complex. Refluxing was continued for 20 min after addition was complete. The mixture was cooled to ambient temperature and methanol saturated with hydrogen chloride was added very slowly until pH 2 was achieved. The mixture was concentrated in vacuo and the residue was dissolved in methanol and concentrated in vacuo again. The solid residue was suspended in 125 mL of ethanol, filtered, rinsed with ethanol then diethyl ether. The white solid was dried in vacuo to afford 25.4 g (40%) of the title compound. The filtrate was concentrated in vacuo and suspended in diethyl ether. The solid was filtered, rinsed with diethyl ether and dried in vacuo to afford another 15.6 g (25%) of the title compound.

Preparation 32

2-(4-Methylphenyl)propionitrile

The title compound was prepared from 4-methylphenyl-acetonitrite as described in Preparation 7.

Analysis for $C_{10}H_{11}N$: Theory: C, 82.72; H, 7.64; N, 9.65. Found: C, 82.75; H, 7.42; N, 9.94.

Preparation 33

2-(4-Methylphenyl)propylamine hydrochloride

The title compound was prepared from the product of Preparation 32 as described in Preparation 8.

Field Desorption Mass Spectrum: M=150 (M–HCl)

Preparation 34

2-(4-Benzyloxyphenyl)propiohitrile

4-Hydroxyphenylacetonitrile (15.3 g, 114.9 mmol) was dissolved in dimethylformamide (120 ml) and to this was added potassium carbonate (23.78 g, 172.4 mmol), benzyl bromide (20.64 g, 120.6 mmol) and potassium iodide (3.81 g, 30.0 mmol). The solution was stirred at ambient temperature for 6 hours after which water was added. 4-Benzyloxyphenyl-acetonitrile precipitated out of solution. The suspension was filtered and the precipitate washed with water (3×). Yield 24.8 g (97%) as yellow crystals. The title product was prepared from 4-benzyloxyphenyl-acetonitrile as described in Preparation 7. Yield 76%.

Field Desorption Mass Spectrum: M=237.2.

Analysis for $C_{16}H_{15}NO$: Theory: C, 80.98; H, 6.37; N, 5.90. Found: C, 80.93; H, 6.46; N, 6.11.

Preparation 35

2-(4-Benzyloxyphenyl)propylamine hydrochloride

The title compound was prepared from the product of Preparation 34 as described in Preparation 2.

Analysis for $C_{16}H_{20}ClNO$: Theory: C, 59.55; H, 8.00; N, 6.94. Found: C, 59.33; H, 7.89; N, 6.71.

Preparation 37

2-(4-bromophenyl)-1-nitro-1-methylethylene

A solution of 30.0 g (162 mmol) of 4-bromobenzaldehyde, 116 mL (1.6 mole) of nitroethane, and 37.5 g (486 mmol) of ammonium acetate in 200 mL of toluene was heated under a Dean and Stark trap for 18 hours. The mixture was then cooled to 80° C., 1 mL of concentrated sulfuric acid was added, and the mixture was stirred at 80° C. for 2 hours. The mixture was then cooled to ambient temperature and washed with 200 mL of brine. The organic layer was separated and the aqueous layer was extracted three times with 60 mL of diethyl ether. The combined organics were dried ($MgSO_4$), filtered and concentrated in vacuo. The residue was recrystallized from methanol to afford 18.7 g (47%) of the title compound.

Preparation 38

2-(4-bromophenyl)-1-nitro-1-methylethane

A suspension of 1.3 g (33.9 mmol) of lithium aluminum hydride in 55 mL of tetrahydrofuran (THF) was cooled to 0° C. A solution of 4.1 g (16.9 mmol) of material from Preparation 37 in 5 mL of THF was added dropwise. 1.3 mL of water, 1.3 mL of 1M sodium hydroxide and 4.0 mL of water were added in sequence. The mixture was filtered through Celite and rinsed with dichloromethane. The organics were concentrated in vacuo to afford 3.0 g of the title compound (83%).

Preparation 41

2-(4-bromophenyl)-N-(t-butoxycarbonyl)ethylamine

To a room temperature solution of 10.0 g (50.0 mmol) of 4-bromophenethylamine and 11.0 g (50.0 mmol) of di-tert-butyl dicarbonate in 100 mL of chloroform was added 100 mL of saturated aqueous sodium bicarbonate. The mixture was stirred at room temperature for 1.5 hours and diluted with 100 mL of water. The organic layer was separated and the aqueous layer was extracted two times with 100 mL each of chloroform. The combined organics were washed once with 100 mL of 10% aqueous sodium bisulfate, dried ($NaSO_4$), filtered and concentrated in vacuo to afford 14.6 g (97%).

Mass Spectrum: M+1=301.

Preparation 42

4-cyanophenylboronic acid

A solution of 10.0 g (54.9 mmol) of 4-bromobenzonitrile in 100 mL of tetrahydrofuran was cooled to −85° C. whereupon 36.0 mL (57.6 mmol) of 1.6M solution of n-butyllithium in hexane was added. The mixture was stirred for five minutes and 19.0 mL (82.4 mmol) of triisopropylborate was added. The mixture was stirred at −85° C. for 30 minutes then warmed to ambient temperature over one hour. To the mixture was added 35 mL of 5 N hydrochloric acid and stirring was continued for 2.5 hours. The mixture was diluted with 100 mL of saturated aqueous sodium chloride and extracted three times with 100 mL each of ethyl ether. The combined organics were dried ($MgSO_4$), filtered and concentrated in vacuo. The residue was recrystallized from water and filtered to afford 2.0 g (25%) of the title compound.

Preparation 45

Dibromoformaldoxime

A solution of 150 g (1.6 mole) of glyoxylic acid and 142 g (2.0 mole) of hydroxylamine hydrochloride in 1200 mL of water was stirred for 2 days. To the mixture was added slowly 342 g (4.1 mole) of sodium bicarbonate and 1000 mL of dichloromethane. The mixture was cooled to 0° C. and a solution of 147 mL (2.8 mole) bromine in 700 mL of dichloromethane was added dropwise. The mixture was stirred at ambient temperature for 18 hr. The organic layer was separated and the aqueous layer was extracted three times with 300 mL each of dichloromethane. The combined organic extracts were dried ($MgSO_4$), filtered and concentrated in vacuo to afforded 93.1 g (28%) of the title compound.

Preparation 46

2-trimethylstannylthiazole

A. To a −78° C. solution of 5.0 g (58.7 mmol) of thiazole in 120 mL of tetrahydrofuran was added of 36.7 mL (58.7 mmol) of a 1.6 M solution of n-butyllithium in hexane. The mixture was stirred for 20 minutes whereupon 11.7 g (58.7 mmol) in 15 mL of tetrahydrofuran was added dropwise over 15 minutes. The cooling bath was removed and the mixture was stirred for two hours. The mixture was diluted with 100 mL of water and extracted three times with 100 mL ethyl ether. The combined organics were dried ($MgSO_4$), filtered and concentrated in vacuo. The residue was dissolved in 50 mL of ethyl ether, filtered through silica gel and concentrated in vacuo to afford 3.6 g (24%) of the title compound.

Preparation 49

4-(4-Bromophenyl)-1,1-dioxotetrahydro-1,2-thiazine

A. Ethyl 4-bromophenylacetate: A solution of 25.0 g (116.3 mmol) of 4-bromophenylacetic acid, 24.1 g (174.4 mmol) of potassium carbonate and 10.2 mL (127.9 mmol) of iodoethane in 250 mL of acetonitrile was heated at 70° C. for 16 hours. The mixture was cooled to ambient temperature, diluted with 200 mL of ethyl acetate and washed once with 200 mL of saturated aqueous sodium bicarbonate. The organic layer was separated and the aqueous layer was extracted three times with 75 mL each of ethyl acetate. The combined organics were dried ($MgSO_4$), filtered and concentrated in vacuo to afford 16.2 g (57%) of the title compound.

B. Phenyl 3-carbethoxy-3-(4-bromophenyl)propylsulfonate: A solution of 16.2 g (66.6 mmol) of material from Step A, 4.6 g (33.3 mmol) of potassium carbonate and 4.4 g (16.7 mmol) of 18-crown-6 in 130 mL of toluene was heated to 90° C. and 6.1 g (33.3 mmol) of phenyl vinylsulfonate in 35 mL of toluene was added dropwise over one hour. The mixture was heated for 16 hours, cooled to ambient temperature and diluted with 100 mL of ethyl acetate. The mixture was washed once with 100 mL of half saturated brine. The organic layer was separated and the aqueous layer was extracted once with 50 mL of ethyl acetate. The combined organics were dried ($MgSO_4$), filtered and concentrated in vacuo. Chromatography (Waters 2000, 15% ethyl acetate/hexane) of the residue affords 4.8 g (17%) of the title compound.

Analysis calculated for $C_{18}H_{19}O_5SBr$: %C, 50.59; %H, 4.48. Found: %C, 50.61; %H, 4.47.

Mass Spectrum: M+1=428.

C. Phenyl 3-carboxy-3-(4-bromophenyl)propylsulfonate: To a solution of 4.8 g (11.3 mmol) of material from Step B in 40 mL of methanol was added 6.8 mL of 2 N aqueous sodium hydroxide. The mixture was stirred at ambient temperature for 5 hours and concentrated in vacuo. The residue was dissolved in 50 mL of water and extracted three times with 20 mL each of ethyl ether. The aqueous layer is acidified to pH 2 with 10% aqueous sodium bisulfate and extracted four times with 20 mL each of ethyl acetate. The combined ethyl acetate layers were dried ($MgSO_4$), filtered and concentrated in vacuo to afford 4.1 g (91%) of the title compound.

Analysis calculated for $C_{16}H_{15}O_5SBr$: %C, 48.13; %H, 3.79. Found: %C, 48.17; %H, 3.53.

Mass Spectrum: M=399.

D. Phenyl 3-carboxamido-3-(4-bromophenyl)propylsulfonate: To a 0° C. solution of 4.1 g (10.2 mmol) of material from Step C and 2.0 mL (14.3 mmol) of triethylamine in 23 mL of tetrahydrofuran was added 1.9 mL (14.3 mmol) of isobutyl chloroformate. The mixture was stirred at 0° C. for 25 minutes whereupon 11.2 mL (22.4 mmol) of a 2 N solution of ammonia in methanol was added. The cooling bath was removed and the mixture stirred for 16 hours. The mixture was diluted with 50 mL of ethyl acetate and washed once with 50 mL of water. The organic layer was separated and the aqueous layer was extracted three times with 25 mL each of ethyl acetate. The combined organics were dried ($MgSO_4$), filtered and concentrated in vacuo. Chromatography (250 g silica gel, 35% acetone/hexane) of the residue affords 1.7 g (44%) of the title compound.

Mass Spectrum: M=398.

E. 4-(4-Bromophenyl)-1,1,3-trioxotetrahydro-1,2-thiazine: To a 0° C. solution of 9.0 mL (9.0 mmol) of a 1.0

M tetrahydrofuran solution of potassium tert-butoxide in 15 mL of tetrahydrofuran was added a solution of 1.7 g (4.5 mmol) of material from Step D in 14 mL of tetrahydrofuran dropwise over 30 minutes. After stirring at 0° C. for two hours, the cooling bath was removed and stirring continued for 30 minutes. The mixture was diluted with 25 mL of water and extracted two times with 10 mL each of ethyl ether. The aqueous portion was acidified to pH 2 with 10% aqueous sodium bisulfate and extracted four times with 20 mL each of ethyl acetate. The combined ethyl acetate layers were dried (MgSO$_4$), filtered and concentrated in vacuo. Chromatography (75 g silica gel, 0.25% acetic acid/40% acetone/hexane) of the residue affords 0.2 g (17%) of the title compound.

Analysis calculated for $C_{10}H_{10}NO_3SBr$: %C, 39.49; %H, 3.31; %N, 4.61. Found: %C, 39.74; %H, 3.23; %N, 4.42.

Mass Spectrum: M=304.

F. To a suspension of 0.13 g (0.4 mmol) of material from Step E and 0.2 g (4.9 mmol) of sodium borohydride in 3 mL of dioxane was added 0.4 mL (4.9 mmol) of trifluoroacetic acid slowly via syringe. After stirring at ambient temperature for 30 minutes the mixture was heated to reflux for 5 hours. The mixture was cooled to ambient temperature, diluted with 3 mL of methanol and stirred for 16 hours. The mixture was removed and stirring continued for 30 minutes. The mixture was concentrated in vacuo, dissolved in 10 mL of ethyl acetate and washed two times with 5 mL each of 1 N hydrochloric acid and once with 5 mL of 20% saturated aqueous sodium bicarbonate/brine. The organics were dried (MgSO$_4$), filtered and concentrated in vacuo to afford 0.1 g (89%) of the title compound.

Analysis calculated for $C_{10}H_{12}NO_3SBr$: %C, 41.39; %H, 4.17; %N, 4.83. Found: %C, 41.10; %H, 4.34; %N, 4.76.

Mass Spectrum: M−1=289.

Preparation 50

D,L-penicillamine methyl ester hydrochloride

Through a suspension of 10.0 g (67.0 mmol) of D,L-penicillamine in 200 mL of methanol was bubbled hydrogen chloride for 5 minutes. The mixture was refluxed for 16 hours, cooled to ambient temperature and concentrated in vacuo The residue was suspended in ethyl ether, filtered and dried to afford 12.6 g (94%) of the title compound.

Mass Spectrum: M=163.

Preparation 51

N-(t-butoxycarbonyl)-4-tributylstannylaniline

A. N-(t-Butoxycarbonyl)-4-bromoaniline: To a solution of 6.0 g (39.4 mmol) of 4-bromoaniline in 30 mL of tetrahydrofuran was added 69.8 mL (69.8 mmol) of a 1.0 M solution of sodium bis(trimethylsilyl)amide in tetrahydrofuran. To the mixture was added 7.6 g (34.9 mmol) of di-t-butyldicarbonate in 10 mL of tetrahydrofuran. The mixture was stirred at ambient temperature for one hour and concentrated in vacuo. The residue was dissolved in 50 mL of ethyl acetate and washed once with 50 mL of 10% aqueous sodium bisulfate. The organic layer was separated and the aqueous layer was extracted two times with 25 mL each of ethyl acetate. The combined organics were dried (MgSO$_4$), filtered and concentrated in vacuo. Chromatography (250 g of silica gel, 10% ethyl acetate/hexane) of the residue afforded 5.0 g (53%) of the title compound.

Analysis calculated for $C_{11}H_{14}NO_2Br$: %C, 48.55; %H, 5.19; %N, 5.15. Found: %C, 48.81; %H, 5.29; %N, 4.95.

Mass Spectrum: M−1=271.

B. A degassed solution of 4.9 g (18.0 mmol) of material from Step A, 2.6 mL (18.9 mmol) of triethylamine, 9.6 mL (18.9 mmol) of bis(tributyltin) and 1.0 g (0.9 mmol) of tetrakis(triphenylphosphine)palladium(0) in 45 mL of toluene was heated to 100° C. for 5 hours. The mixture was cooled to ambient temperature and diluted with 40 mL of ethyl acetate. The mixture was washed once with 50 mL of 10% aqueous sodium bisulfate, the organics separated and the aqueous layer extracted three times with 20 mL each of ethyl acetate. The combined organics were dried (MgSO$_4$), filtered and concentrated in vacuo. Chromatography (400 g of silica gel, 5% ethyl acetate/hexane) of the residue afforded 1.4 g (16%) of the title compound.

Mass Spectrum: M+1=483.

Preparation 52

N-2-(4-tri-n-butylstannylphenyl)propyl methanesulfonamide

The title compound (3.6 g) was prepared by the method of Preparation 40 starting from the product of Example 1.

Preparation 53

N-2-(4-(3-thienyl)phenyl)propyl amine

A. 2-(3-thienyl)phenyl-N-(t-butoxycarbonyl)propyl amine: To a solution of 0.7 g (2.2 mmol) of material from Preparation 4, 0.3 g (2.4 mmol) thiophene-3-boronic acid and 0.46 g (3.3 mmol) of potassium carbonate in 5 mL of dioxane and 1 mL of water was added 0.025 g (0.11 mmol) of palladium(II)acetate and 0.058 g (0.22 mmol) triphenylphosphine. The mixture was heated at 100° C. for 18 hr. The mixture was cooled to room temperature and 5 mL of brine was added. The organic layer was separated and dried (MgSO$_4$), filtered and concentrated in vacuo. Chromatography (25 g of silica gel, 25% ethyl acetate/hexane) of the residue afforded 0.44 g (60%) of the title compound.

B. A solution of 0.4 g (1.3 mmol) of material from Preparation 53A in 4 mL of dichloromethane and 1 mL of trifluoroacetic acid was stirred at ambient temperature for 3 hr. The mixture was concentrated in vacuo and the residue was dissolved in 5 mL ethyl acetate and 5 mL saturated sodium bicarbonate. The organic layer was separated and the aqueous layer extracted three times with 5 mL of ethyl acetate. The combined organics were dried (MgSO$_4$), filtered and concentrated in vacuo to afford 0.21 g (74%) of the title compound.

Preparation 54A 4-(N,N-dibenzylamino)phenylacetonitrile

A solution of 4-aminophenylacetonitrile (20 g, 151.3 mmol) in dry DMF (150 ml) was treated with potassium carbonate (50.1 g, 363.1 mmol), benzyl bromide (54.4 g, 318 mmol), and potassium iodide (5 g, 0.2 30.3 mmol). The reaction mixture was stirred at room temperature for 12 h. Water (100 ml) was added to the mixture and the organic was extracted with ether (3×200 ml). The combined organic fraction was washed with brine (200 ml), dried over sodium sulfate and concentrated. The crude product was further purified by flash chromatography (SiO$_2$, 20% EtOAc:Hexanes) to give 36.2 g (76%) of the pure product. NMR was consistent with the proposed title structure. Field Desorption Mass Spectrum: M$^+$=312.

Preparation 55

2-(4-(N,N-dibenzylamino)phenyl)propionitrile

A −78° C. solution of the material from Preparation 54A (22.8 g, 73 mmol) in dry THF (70 ml) was treated with lithium bis(trimethylsilyl)amide (1M in THF, 76.6 ml, 76.6 mmol). The resulting mixture was stirred at −78° C. for 1 h. Methyl iodide (4.8 ml, 76.6 mmol) was added to the mixture. The reaction mixture was stirred at −78° C. for 1 h and gradually was allowed to warm to room temperature over 12 h. Hydrochloric acid (0.2 M, 100 ml) was added to the mixture and the organic was extracted with ether (3×200 ml). The combined organic fraction was washed with water (3×200 ml), brine (200 ml), dried over sodium sulfate and concentrated. The crude product was further purified by flash chromatography ($SiO_2$, 20% EtOAc:Hexane) to give 22.6 g (95%) of the pure product. NMR was consistent with the proposed title structure. Field Desorption Mass Spectrum: $M^+$=326.

Preparation 56

2-(4-(N,N-dibenzylamino)phenyl)propylamine hydrochloride

A 0° C. solution of the material from Preparation 55 (23.6 g, 72.3 mmol) in dry THF (100 ml) was treated with borane methylsulfide (10 M in THF, 8 ml, 80 mmol). The reaction mixture was stirred while refluxing for 3 h. The solution was cooled down to room temperature and was treated with a saturated solution of hydrochloric acid in methanol until a white precipitate formed. The solvent was removed in vacuo and the resulting white solid was triturated with ether (4×100 ml). The desired hydrochloric salt was dried under vacuo to give 28.2 g (97%) of the pure product which was used in next step without any further purification. NMR was consistent with the proposed title structure.

Preparation 61

2-(4-nitrophenyl)propionitrile

A −15° C. solution of 4-nitroacetophenone (16.5 g, 100 mmol) and tosylmethyl isocyanide (29.3 g, 150 mmol) in methoxyethyl ether (400 ml) was slowly treated with a room temperature solution of the potassium t-butoxide (28 g, 250 mmol) in t-butanol (200 ml). The reaction mixture was stirred at −15° C. for 1 h and then allowed to warm to room temperature over night. Water (100 ml) was added to the mixture and organic was extracted with ether (3×200 ml). The combined organic fraction was washed with water (3×200 ml), brine (100 ml), dried over sodium sulfate, and concentrated in vacuo to give the crude material which was further purified by flash chromatography ($SiO_2$, 30% EtOAc:Hexane) to give 13.6 g (77%) of the title compound. NMR was consistent with the proposed title structure. Field Desorption Mass Spectrum: $M^+$=225.

Preparation 62

2-(4-nitrophenyl)propylamine

A 0° C. solution of the material from Preparation 61 (11.8 g, 67 mmol) in dry THF (200 ml) was treated with borane tetrahydrofuran (1 M in THF, 72 ml, 72 mmol). The reaction mixture was stirred at room temperature for 16 h. A solution of THF:MeOH (1:1, 10 ml)and sodium hydroxide (5 N, 40 ml) were added to the reaction mixture stepwise and the mixture was refluxed for 5 h. The reaction mixture was allowed to cool to room temperature. Organic was extracted with dichloromethane (3×100 ml). The combined organic fraction was washed with water (3×200 ml), brine (100 ml), dried over potassium carbonate, and concentrated in vacuo to give the crude material which was further purified by flash chromatography ($SiO_2$, 5% MeOH:$CH_2Cl_2$) to give 8.5 g (71%) of the pure product. NMR was consistent with the proposed title structure. Field Desorption Mass Spectrum: $M^+$=181.

Preparation 68

N-t-butyloxycarbonyl-4-piperazinoacetophenone

A solution of the 4-piperazinoacetophenone (10 g, 49 mmol) in tetrahydrofuran:water (200 ml, 1:1 mixture) was treated with potassium carbonate (8.43 g, 58 mmol) and di-t-butyl dicarbonate (13.1 g, 53.9 mmol). The reaction mixture was stirred at room temperature for 3 h. Water (300 ml) was added to the mixture and organic was extracted with ethyl acetate (3×100 ml). The combined organic fraction was washed with water (2×200 ml), brine (100 ml), dried over sodium sulfate, and concentrated in vacuo to 17.41 g of the yellowish solid. The crude product was further purified by Prep LC 2000 eluting with 30% EtOAc:Haxanes to give 10.9 g (73%) of the title compound as a white solid. Field Desorption Mass Spectrum: $M^+$=305.

Preparation 69

2-(N-t-butyloxycarbonyl-4-piperazinophenyl) propionitrile

The title compound 1.8 g (16%) was prepared as a solid following the method of Preparation 61, starting from the product of Preparation 68 and using tosylmethyl isocyanide. NMR was consistent with the proposed title structure. Field Desorption Mass Spectrum: $M^+$=316.

Preparation 70

2-(N-t-butyloxycarbonyl-4-piperazinophenyl) propylamine

The title compound 1.78 g (100%) was prepared as a solid following the method of Preparation 62, starting from the product of Preparation 69 and using borane methylsulfide. NMR was consistent with the proposed title structure. Field Desorption Mass Spectrum: $M^+$=319.

Preparation 74

3-Tributyltin-2-cyclopenten-1-one

A −20° C. solution of hexabutylditin (4.6 g, 7.9 mmol) in dry THF (15 ml) was treated with nBuLi (4.9 ml, 7.9 mmol, 1.6 M solution in hexanes). The reaction, mixture was stirred at −20° C. for 30 minutes and then cooled to −78° C. The mixture was treated with 3-ethoxy-2-cyclopenten-1-one (1.0 g, 7.9 mmol) and the reaction mixture stirred at −78° C. for 30 minutes. A saturated, aqueous solution of ammonium chloride (2 ml) followed by water (30 ml) and the organic extracted with hexanes (2×30 ml). The combined organic layers were washed with brine (20 ml), dried over magnesium sulfate and concentrated in vacuo. This gave 2.7 g (93%) of the crude product which was used without further purification. NMR was consistent with the title structure.

Preparation 76

1-(4-bromophenyl)-2,5-dimethylpyrrole

4-Bromoaniline (56.0 g., 0.33 Mol.), 2,5-hexanedione (37.6 g., 0.33 Mol), and acetic acid (5 ml) were placed into Toluene (500 ml) and heated under reflux for 8 hours employing a dean stark trap to remove the water from the reaction. The reaction was cooled to room temperature and concentrated under reduced vacuum. The resulting oil was taken into ethyl acetate, washed one time each with 2N hydrochloric acid, 2N NaOH, and $H_2O$, dried over $Na_2SO_4$, and concentrated under reduced vacuum to yield a brown solid. Material was purified by silica gel flash chromatography eluting with hexane. Concentration of the appropriate fractions yielded 55.0 gm. of a light yellow solid. (68%) NMR was consistent with the proposed title structure. Field Desorption Mass Spectrum: $M^+$ 249 m.p. 71°–73° C.

Preparation 77

1-(4-acetylphenyl)-2,5-dimethylpyrrole

A –30° C. solution of the material from Preparation 76 (25.0 g, 0.1 mol) in dry ether (500 ml) was treated with n-butyllithium (70 ml of 1.6 M, 0.12 mol) and stirred for one hour at –30° C. N,N Dimethyl acetamide (9.7 g, 0.12 mol) was added and the reaction continued at this temperature for 4 hours. The reaction was then allowed to warm to room temperature and stirred over night at this temperature. In the morning, the mixture was diluted with ethyl acetate and the combined organic layers were washed one time each with 2.0 N hydrochloric acid and $H_2O$, dried over $Na_2SO_4$, and concentrated under reduced vacuum to yield a white solid. The material was triturated in hexane and filtered to yield 12.8 gm. of a white solid. m.p. 106°–108° C. (60%) NMR was consistent with the proposed title structure. Field Desorption Mass Spectrum: $M^+$ 214

Preparation 78

1-(4-(1-cyano)ethylphenyl)-2,5-dimethylpyrrole

The starting ketone from Preparation 77 (44.3 g, 0.21 mol), tosylmethyl isocyanide (40.6 g, 0.21 mol), potassium-t-butoxide (39.2 g, 0.35 mol), and t-butyl alcohol (250 ml) were reacted in ethylene glycol dimethyl ether (500 ml) as described in Preparation 61 to yield a yellow solid. Purification was achieved by silica gel flash chromatography eluting with hexanelethyl acetate 4:1 to yield 32.3 gm. of yellow crystals. m.p. 79°–80° C. (68%) Field desorption Mass Spectrum: $M^+$ 225

Preparation 79

1-(4-(2-(2-cyano)propyl)phenyl)-2,5-dimethylpyrrole

A –78° C. solution of material from Preparation 78 (7.0 g, 32 mmol) in dry tetrahydrofuran (100 ml) was treated with lithium(bis)trimethylsilylamide (40 ml of 1.0M, 1.3 eq.). After stirring 30 minutes at this temperature, methyl iodide (2.6 ml, 1.3 eq.) was added dropwise and the reaction was allowed to warm to room temperature. The mixture was diluted with ether and the combined organic layers were washed once with $H_2O$, dried over $K_2CO_3$, and concentrated under reduced vacuum to yield 7.61 gm. of a yellow solid. Material was purified via silica gel chromatography eluting with a solvent of hexane/ethyl acetate 9:1 to yield 6.30 gm. of a yellow solid. m.p. 135°–137° C. (83%). Field desorption Mass Spectrum: $M^++1$ 239

Preparation 80

1-(4-(2-(3-amino-2-methyl)propyl)phenyl-2,5-dimethylpyrrole

The nitrite from Preparation 79 (6.23 g, 26.2 mmol) in tetrahydrofuran (250 ml) was treated with borane-THF complex (17.1 ml, 1.0 M) as described in Preparation 62 to yield 6.37 gm. of a foam. This material was purified via silica gel chromatography eluting with a gradient solvent of dichloromethane to dichloromethane/methanol 9:1 to yield 4.08 gm. of a white solid. m.p. 95°–97° C. (65%). NMR was consistent with the proposed title structure. Field Desorption Mass Spectrum: $M^+$ 243

Preparation 85

4-Bromophenylacetyl chloride

A solution of 50.0 g (232 mmol) of 4-bromophenyl-acetic acid in 150 mL of thionyl chloride was stirred at room temperature for 18 hr. The mixture was concentrated in vacuo to afford 54 g (100%) of the title compound.

Preparation 86

(R)-(–)-4-Benzyl-3-(4-bromophenylacetyl)-2-oxazolidinone

A solution of 20.0 g (117 mmol) of (R)-(+)-4-benzyl-2-oxazolidinone in 300 mL of tetrahydrofuran was cooled to –78° C. and 73.0 mL (117 mmol) of 1.6M n-Butyllithium was added dropwise. The mixture was stirred 30 min then was slowly added via cannula to a solution of 25 g (107 mmol) of material from Preparation 85 in 150 mL of tetrahydrofuran at –78° C. The mixture was stirred for 1 hr and then 300 mL of 10% aqueous sodium bisulfate was added. The organic layer was separated and the aqueous layer was extracted three times with 100 mL each of ether. The combined organic extracts were dried ($MgSO_4$), filtered and concentrated in vacuo. Chromatography (750 g of silica gel, 25% ethyl acetate/hexane) of the residue afforded 27.4 g (68%) of the title compound.

Analysis calculated for $C_{18}H_{16}BrNO_3$: %C, 57.77; %H, 4.31; %N, 3.74. Found: %C, 57.62; %H, 4.21; %N, 3.74.

Field Desorption Mass Spectrum: M=374.

$[\alpha]_D^{20}$=–59.83 (c=1.04, $CHCl_3$).

Preparation 87

(–)-4R-Benzyl-3-(2R-(4-bromophenyl)propionyl)-2-oxazolidinone

A solution of 48 g (128 mmol) of material from Preparation 86 in 200 mL of tetrahydrofuran was cooled to –78° C. and 141 mL (141 mmol) of 1M sodium bis(trimethylsilyl)amide was added dropwise. The mixture was stirred 60 min then a solution of 20 g (141 mmol) of iodomethane in 20 mL of tetrahydrofuran was slowly added. The mixture was stirred for 60 min at –78° C. and then allowed to warm to room temperature for 60 min. To the reaction was added 10% aqueous sodium bisulfate and the organic layer was separated and the aqueous layer was extracted three times with 100 mL each of ether. The combined organic extracts were dried ($MgSO_4$), filtered and concentrated in vacuo. Chromatography (500 g of silica gel, 25% ethyl acetate/hexane) of the residue afforded 28.7 g (58%) of the title compound.

Analysis calculated for $C_{19}H_{18}BrNO_3$: %C, 58.78; %H, 4.67; %N, 3.61. Found: %C, 58.81; %H, 4.63; %N, 3.54.

Field Desorption Mass Spectrum: M=388.

$[\alpha]_D^{20}$=–110.4 (c=0.96, $CHCl_3$).

Preparation 88

(R)-(+)-2-(4-bromophenyl)propanol

A solution of 28.7 g (74 mmol) of material from Preparation 87 in 250 mL of ether was cooled to 0° C. and 74 mL (148 mmol) of 2M lithiumborohydride in tetrahydrofuran was added dropwise. The mixture was stirred. for 2 hr then 1N sodium hydroxide was added and the mixture was stirred until both organic and aqueous layers became clear. The organic layer was separated and the aqueous layer was extracted three times with 10 mL each of ethyl acetate. The combined organic extracts were dried ($MgSO_4$), filtered and concentrated in vacuo. Chromatography (800 g of silica gel, 25% ethyl acetate/hexane) of the residue afforded 12.3 g (79%) of the title compound.

Analysis calculated for $C_9H_{11}BrO$: %C, 50.26; %H, 5.15. Found: %C, 48.96; %H, 4.91.

Field Desorption Mass Spectrum: M+1=216.

$[\alpha]_D^{20}$=+13.79 (c=1.06, $CHCl_3$).

Preparation 90

(R)-2-(4-bromophenyl)propyl azide

A solution of 15.8 g (54 mmol) of material from Preparation 89 in 180 mL of N,N-dimethylformamide and 7.0 g (108 mmol) sodium azide was heated at 80° C. for 5 hr. The mixture was cooled and concentrated in vacuo. The residue was partitioned between 100 mL of water and 100 mL of ether. The organic layer was separated and the aqueous layer was washed three times with 30 mL each of ether. The combined organic extracts were dried ($MgSO_4$), filtered and concentrated in vacuo to afforded 12.13 g (94%) of the title compound.

Preparation 91

(R)-(+)-2-(4-bromophenyl)propyl amine hydrochloride

A solution of 12.2 g (50.4 mmol) of material from Preparation 90 and 14.5 g (55.4 mmol) of triphenylphosphine in 168 mL of tetrahydrofuran and 3.6 mL of water was stirred at room temperature for 18 hr. The mixture was diluted with 100 mL of ether and 50 mL of brine. The organic layer was removed and dried ($MgSO_4$), filtered and concentrated in vacuo, The residue was dissolved in 100 mL of ether and to this was added 200 mL of hydrochloric acid saturated ether. Filtration of the resulting solid afforded 11.9 g (94%) of the title compound.

Analysis calculated for $C_9H_{13}BrClN$: %C, 43.14; %H, 5.23; %N, 5.59. Found: %C, 43.44; %H, 5.23; %N, 5.56.

Mass Spectrum: [M−HCl]=214.

$[\alpha]_D^{20}$=+24.06 (c=1.00, $H_2O$).

Preparation 92

(R)-2-(4-bromophenyl)-N-(t-butoxycarbonyl)propyl amine

To a solution of 5.0 g (20.0 mmol) of material from Preparation 91 in 30 mL of chloroform and 30 mL of saturated sodium bicarbonate was added 4.3 g (20.0 mmol) of di-tertbutyl dicarbonate. The solution was stirred at room temperature for18 hr. The organic layer was separated and the aqueous layer was extracted three times with 10 mL each of chloroform. The combined organic extracts were dried ($MgSO_4$), filtered and concentrated in vacuo to afford 6.2 g (100%) of the title compound.

Preparation 93

(S)-(+)-4-Benzyl-3-(4-bromophenylacetyl)-2-oxazolidinone

Following the procedure of Preparation 86 and using (S)-(−)-4-benzyl-2-oxazolidinone instead of (R)-(+)-4-benzyl-2-oxazolidinone afforded 25.3 g (63%) of the title compound.

Analysis calculated for $C_{18}H_{16}BrNO_3$: %C, 57.77; %H, 4.31; %N, 3.74. Found: %C, 57.69; %H, 4.18; %N, 3.82.

Field Desorption Mass Spectrum: M=374.

$[\alpha]_D^{20}$=+59.35 (c=1.04, $CHCl_3$).

Preparation 94

(+)-4S-Benzyl-3-(2S-(4-bromophenyl)propionyl)-2-oxazolidinone

Following the procedure of Preparation 87 and using material from Preparation 93 instead of material from Preparation 86 afforded 28.9 g (51%) of the title compound.

Analysis calculated for $C_{19}H_{18}BrNO_3$: %C, 58.78; %H, 4.67; %N, 3.61. Found: %C, 59.40; %H, 4.61; %N, 3.64.

Field Desorption Mass Spectrum: M=388.

$[\alpha]_D^{20}$=+114.8 (c=1.01, $CHCl_3$).

Preparation 95

(S)-(−)-2-(4-bromophenyl)propanol

Following the procedure of Preparation 88 and using material from Preparation 94 instead of material from Preparation 87 afforded 12.3 g (79%) of the title compound.

Analysis calculated for $C_9H_{11}BrO$: %C, 50.26; %H, 5.15. Found: %C, 50.38; %H, 5.08.

Field Desorption Mass Spectrum: M+1=216.

$[\alpha]_D^{20}$=−13.25 (c=1.06, $CHCl_3$).

Preparation 97

(S)-2-(4-bromophenyl)propyl azide

Following the procedure of Preparation 90 and using material from Preparation 96 instead of material from Preparation 89 afforded 13.0 g (94%) of the title compound.

Preparation 98

(S)-(−)-2-(4-bromophenyl)propyl amine hydrochloride

Following the procedure of Preparation 91 and using material from Preparation 97 instead of material from Preparation 90 afforded 11.6 g (86%) of the title compound.

Analysis calculated for $C_9H_{13}BrClN$: %C, 43.14; %H, 5.23; %N, 5.59. Found: %C, 43.36; %H, 5.39; %N, 5.64.

Mass Spectrum: [M−HCl]=214.

$[\alpha]_D^{20}$=−25.3 (c=1.02, $H_2O$).

Preparation 99

(S)-2-(4-bromophenyl)-N-(t-butoxycarbonyl)propyl amine

Following the procedure of Preparation 92 and using material from Preparation 98 instead of material from Preparation 91 afforded 5.9 g (94%) of the title compound.

Preparation 100

(R)-2-(4-(3-thienyl)phenyl)-N-(t-butoxycarbonyl) propyl amine

To a solution of 2.0 g (6.4 mmol) of material from Preparation 92, 0.9 g (7.0 mmol) of thiophene-3-boronic acid and 1.3 g (9.6 mmol) of potassium carbonate in 20 mL of dioxane and 5 mL of water was added 0.4 g (0.32 mmol)

of tetrakis(triphenylphosphine)palladium(0). The mixture was heated at 100° C. for 18 hr. The mixture was cooled to room temperature and 20 mL of water and 20 mL of ether was added. The organic layer was separated and the aqueous layer was extracted three times with 10 mL each of ether. The combined organic extracts were dried (MgSO$_4$), filtered and concentrated in vacuo. Chromatography (150 g of silica gel, 15% ethyl acetate/hexane) of the residue afforded 1.4 g (70%) of the title compound.

Preparation 101

(S)-2-(4-(3-thienyl)phenyl)-N-(t-butoxycarbonyl) propyl amine

Following the procedure of Preparation 100 and using material from Preparation 99 instead of material form Preparation 92 afforded 5.9 g (94%) of the title compound.

Preparation 102

2R-(4-(3-thienyl)phenyl)propyl amine

A solution of 1.4 g of material from Preparation 100 in 15 mL 25% trifluoroacetic acid/dichloromethane was stirred at room temperature for 3 hr. The mixture was concentrated in vacuo and the residue was dissolved in 20 mL of 1N sodium hydroxide and 20 mL of ethyl acetate. The organic layer was separated and the aqueous layer was extracted four times with 10 mL each of ethyl acetate. The combined organic extracts were dried (MgSO$_4$), filtered and concentrated in vacuo to afford 0.85 g (89%) of the title compound.

Preparation 103

2S-(4-(3-thienyl)phenyl)propyl amine

Following the procedure of Preparation 102 and using material from Preparation 101 instead of material from Preparation 100 afforded 0.9 g (94%) of the title compound.

Preparation 104

2-(4'-(2-fluorobiphenyl))ethylamine

A. (2-(4-bromophenyl)-N-(t-butoxycarbonyl)ethylamine: To a solution of 10.0 g (50.0 mmol) of 4-bromophenethylamine in 100 mL of chloroform and 100 mL of saturated sodium bicarbonate was added 11.0 g (50.0 mmol) of di-tert-butyl dicarbonate. The solution was stirred at ambient temperature for 1 hour. The organic layer was separated and the aqueous layer was extracted three times with 30 mL each of chloroform. The combined organic extracts were dried (MgSO$_4$), filtered and concentrated in vacuo to afford 15 g (100%) of the title compound.

B. 2-(4-(2-fluorophenyl)phenyl)-N-(t-butoxycarbonyl)-phenyl ethylamine: To a degassed solution of 7.9 g (26.2 mmol) of material from Step A, 5.5 g (39.3 mmol) of material from Preparation 3 and 5.4 g (39.3 mmol) of potassium carbonate in 90 mL of toluene was added 1.5 g (1.3 mmol) of tetrakis(triphenylphosphine)palladium(0). The mixture was heated at 90° C. for 3 hours. The mixture was cooled to ambient temperature and 90 mL of water was added.

The organic layer was separated and the aqueous layer was extracted three times with 30 mL each of ethyl acetate. The combined organic extracts were dried (MgSO$_4$), filtered and concentrated in vacuo. Chromatography (400 g of silica gel, 15% ethyl acetate/hexane) of the residue afforded 7.1 g of material that was triturated in hexane to afford 3.5 g (42%) of the title compound.

C. 2-(4'-(2-fluorobiphenyl))ethylamine: A solution of 3.5 g of material from Step B in 40 mL 20% trifluoroacetic acid/dichloromethane was stirred at ambient temperature for 1 hour. The mixture was concentrated in vacuo to afford 3.9 g (100%) of the title compound.

EXAMPLE 1

Preparation of diethyl N-2-(4-(3-thienyl) phenylpropyl)phosphoramidate

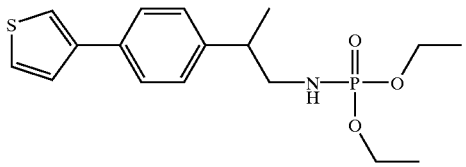

A. Preparation of N-2-(4-(3-thienyl)phenyl)-N-t-butoxycarbonylpropyl amine: To a degassed solution of 8.2 g (26.0 mmol) of material from Preparation 4, 4.0 g (31.2 mmol) of thiophene-3-boronic acid and 5.3 g (39.0 mmol) of potassium carbonate in 75 mL of dioxane and 25 mL of water was added 1.5 g (1.3 mmol) of tetrakis(triphenylphosphine)palladium(0). The mixture was heated at 90° C. for 18 hr. The mixture was cooled to ambient temperature and 200 mL of water and 100 mL of ether was added. The organic layer was separated and the aqueous layer was extracted three times with 60 mL each of ether. The combined organic extracts were dried over anhydrous magnesium sulfate, filtered and concentrated in vacuo. Chromatography (500 g of silica gel, 10% ethyl acetate/hexane) of the residue afforded 7.8 g (94%) of the title compound.

B. Preparation of 2-(4-(3-thienyl)phenyl)propylamine: A solution of 2.3 g (7.2 mmol) of material from part A in 20 mL of dichloromethane and 5 mL of trifluoroacetic acid was stirred at room temperature for three hours. The mixture as concentrated in vacuo and the residue was dissolved in 20 mL of ethyl acetate. This solution was washed once with saturated aqueous sodium bicarbonate. The organic portion was separated and the aqueous portion was extracted four times with 10 mL each of ethyl acetate. The combined organics were dried over anhydrous magnesium sulfate, filtered and concentrated in vacuo to afford 1.5 g (100%) of the title compound.

C. To a 0° C. solution of 0.3 g (1.4 mmol) of material from part B and 0.15 g (1.5 mmol) of triethylamine in 5 mL of dichloromethane was added 0.2 g (1.4 mmol) of diethyl chlorophosphate and the mixture was stirred and allowed to warm to room temperature over four hours. To the mixture was added 5 mL of 1 N hydrochloric acid. The organic portion was separated and the aqueous portion was extracted three times with 5 mL of dichloromethane. The combined organics were dried over anhydrous magnesium sulfate, filtered and concentrated in vacuo. Chromatography (25 g silica gel, ethyl acetate) afforded 0.2 g (35%) of the title compound.

Analysis calculated for $C_{17}H_{24}NO_3PS \cdot 0.2CHCl_3$: %C, 54.76; %H, 6.47; %N, 3.71. Found: %C, 54.39; %H, 6.67; %N, 3.67.

Electrospray Mass Spectrum: M+1=354.

EXAMPLE 2

Preparation of diethyl N-2-(4-(2-fluorophenyl)phenylpropyl phosphoramidate

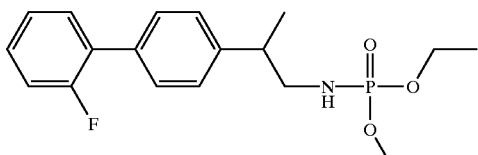

To a 0° C. solution of 0.5 g (2.2 mmol) of material from Preparation 6 and 0.2 g (2.4 mmol) of triethylamine in 5 mL of dichloromethane was added 0.4 g (2.2 mmol) of diethyl chlorophosphate. The mixture was stirred for one hour at 0° C., then allowed to warm to room temperature over 16 hours. The reaction mixture was washed once with 5 mL of 10% aqueous sodium bisulfate. The organic portion was separated and the aqueous portion was extracted two times with 3 mL each of dichloromethane. The combined organics were dried over anhydrous sodium sulfate, filtered and concentrated in vacuo. Chromatography (50 g silica gel, ethyl acetate) of the residue affords 0.3 g (33%) of the title compound.

Analysis calculated for $C_{19}H_{25}NO_3PF$: %C, 62.46; %H, 6.90; %N, 3.83. Found: %C, 62.43, %H, 6.76; %N, 4.13.

Electrospray Mass Spectrum: M=365.

Additional compounds of the present invention include but are not limited to those listed in Table I. The compounds illustrated in Table I can be readily prepared by one of ordinary skill in the art using standard techniques and methods well known in the art in a manner analogous to the procedures described herein from readily available starting materials and from starting materials specifically described hereinabove. As used in Table I, the term "Ex." refers to the Example number, "Prep." refers to Preparation number, and "S.M." refers to a source for starting material. It is recognized by one of ordinary skill in the art that the starting material indicated may require one or more manipulations prior to use in Scheme I, such as deprotection of the amine under standard deprotection conditions as described, for example, by T. W. Green, "Protective Groups in Organic Synthesis", John Wiley & Sons Inc., (1981), Chapter 7; oxidation of a hydroxy substituent under standard oxidizing conditions as described, for example, by J. March, "Advanced Organic Chemistry: Reactions, Mechanisms, and Structure," $2^{nd}$ Edition, McGraw-Hill Inc., (1977), pages 1082–1084; or reduction of a carbonyl, nitro or amide functionality as described, for example, by J. March, "Advanced Organic Chemistry: Reactions, Mechanisms, and Structure," $2^{nd}$ Edition, McGraw-Hill Inc., (1977), pages 1116–1126. Additional known reactions useful for preparing the compounds of the present invention, in addition to those reactions described hereinabove, include the Grignard Reaction, as described by J. March, "Advanced Organic Chemistry: Reactions, Mechanisms, and Structure," $2^{nd}$ Edition, McGraw-Hill Inc., (1977), pages 836–841, and standard amidation reactions, as described by J. March, "Advanced Organic Chemistry: Reactions, Mechanisms, and Structure," $2^{nd}$ Edition, McGraw-Hill Inc., (1977), pages 382–388.

TABLE I formula Ia $$Q-\underset{H}{N}-\underset{\underset{OEt}{|}}{\overset{\overset{O}{\|}}{P}}-OEt$$

| Ex. | Q | S.M. |
|---|---|---|
| 3 | Br—C6H4—CH(CH3)CH2— | Prep. 2 |
| 4 | 3-F-C6H4—C6H4—CH(CH3)CH2— | Ex. 3 |
| 5 | 3-CHO-C6H4—C6H4—CH(CH3)CH2— | Ex. 3 |
| 6 | 4-CHO-C6H4—C6H4—CH(CH3)CH2— | Ex. 3 |

TABLE I-continued
formula Ia
Q—N(H)—P(=O)(OEt)(OEt)
| Ex. | Q | S.M. |
|---|---|---|
| 7 | 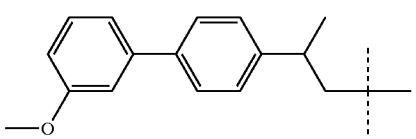 | Ex. 3 |
| 8 | 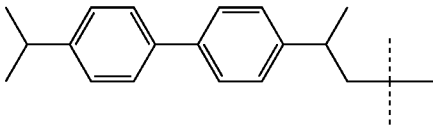 | Prep. 8 |
| 9 | 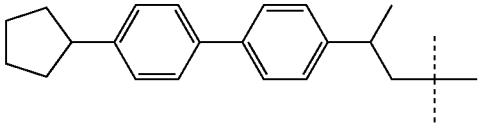 | Ex. 3 |
| 10 | 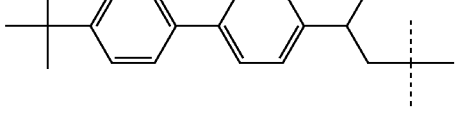 | Prep. 23 |
| 11 | 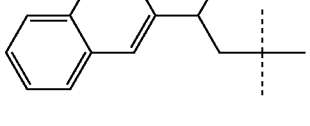 | Prep. 26 |
| 12 | 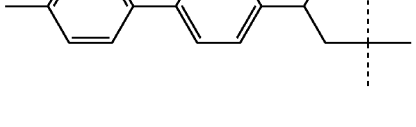 | Ex. 3 |
| 13 |  | Prep. 10 |
| 14 | 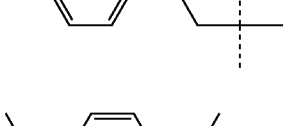 | Prep. 33 |
| 15 | 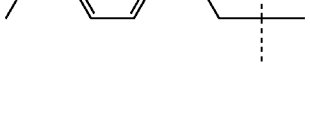 | Prep. 8 |

TABLE I-continued formula Ia $$Q-\underset{H}{N}-\underset{\underset{OEt}{|}}{\overset{\overset{O}{\|}}{P}}-OEt$$

| Ex. | Q | S.M. |
|---|---|---|
| 16 | cyclohexyl-C6H4-CH(CH3)CH2C(CH3)2– | Ex. 3 |
| 17 | 2-chloro-4-[CH(CH3)CH2C(CH3)2–]-piperidinophenyl | |
| 18 | 4-piperidinophenyl-CH(CH3)CH2C(CH3)2– (R) | Synthesis, 6, 447 (1991). |
| 19 | 4-piperidinophenyl-CH(CH3)CH2C(CH3)2– (S) | Synthesis, 6, 447 (1991). |
| 20 | PhCH2O-C6H4-CH(CH3)CH2C(CH3)2– | Prep. 35 |
| 21 | H2N-CH2CH2-C6H4-C6H4-CH(CH3)CH2C(CH3)2– | Ex. 3 |
| 22 | PhCH2O-C6H4-CH(CH3)CH2C(CH3)2– | Ex. 6 (reduction) |
| 23 | NC-C6H4-CH(CH3)CH2C(CH3)2– | Ex. 3 |
| 24 | 2-furyl-C6H4-CH(CH3)CH2C(CH3)2– | Ex. 3 |

TABLE I-continued formula Ia $$Q-\underset{H}{N}-\underset{\underset{OEt}{\overset{O}{\|}}}{P}-OEt$$

| Ex. | Q | S.M. |
|---|---|---|
| 25 | thiazol-2-yl–C₆H₄–CH(CH₃)CH₂C(CH₃)₂– | Ex. 24 |
| 26 | NC–C₆H₄–C₆H₄–CH(CH₃)CH₂C(CH₃)₂– | Prep. 42<br>Ex. 3 |
| 27 | 3-(HO-CH(CH₃))–C₆H₄–C₆H₄–CH(CH₃)CH₂C(CH₃)₂– | Ex. 5<br>(Grignard Reaction) |
| 28 | 3-(HO-CH(CH₂CH₃))–C₆H₄–C₆H₄–CH(CH₃)CH₂C(CH₃)₂– | Ex. 5<br>(Grignard Reaction) |
| 29 | HOOC–C₆H₄–C₆H₄–CH(CH₃)CH₂C(CH₃)₂– | Ex. 3 |
| 30 | H₂N–C(O)–C₆H₄–C₆H₄–CH(CH₃)CH₂C(CH₃)₂– | Ex. 30<br>(amidation) |
| 31 | CH₃NH–C(O)–C₆H₄–C₆H₄–CH(CH₃)CH₂C(CH₃)₂– | Ex. 30<br>(amidation) |
| 32 | (CH₃)₂N–C(O)–C₆H₄–C₆H₄–CH(CH₃)CH₂C(CH₃)₂– | Ex. 30<br>(amidation) |
| 33 | CH₃–C(O)–C₆H₄–C₆H₄–CH(CH₃)CH₂C(CH₃)₂– | Ex. 3 |

TABLE I-continued
formula Ia
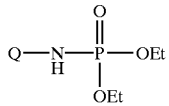
| Ex. | Q | S.M. |
|---|---|---|
| 34 | 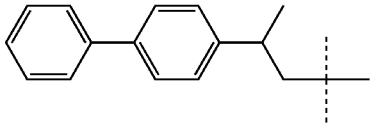 | Ex. 3 |
| 35 | 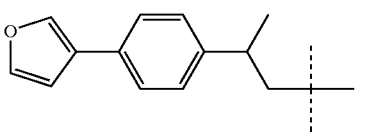 | Ex. 3 |
| 36 | 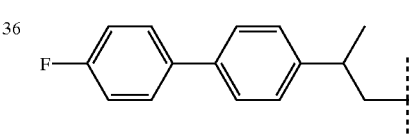 | Ex. 3 |
| 37 | 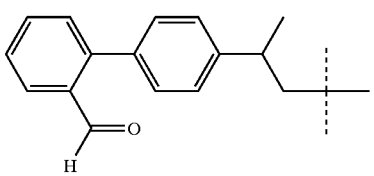 | Ex. 3 |
| 38 | 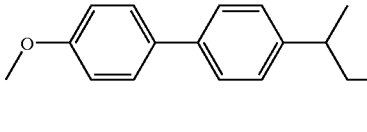 | Ex. 3 |
| 39 | 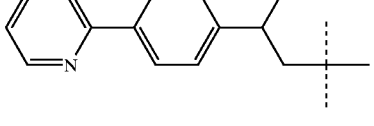 | Ex. 3 |
| 40 | 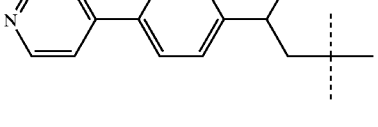 | Ex. 3 |
| 41 | 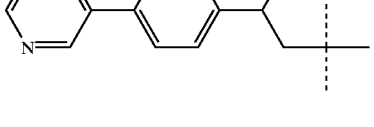 | Ex. 3 |
| 42 | 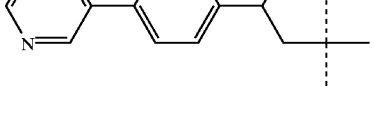 | Ex. 3 |

TABLE I-continued
formula Ia
Q—N(H)—P(=O)(OEt)(OEt)
| Ex. | Q | S.M. |
|---|---|---|
| 43 | 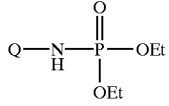 | Ex. 3 |
| 44 | 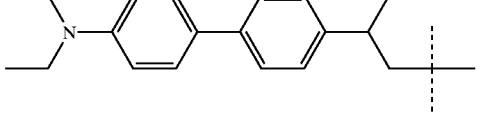 | Ex. 3 |
| 45 | 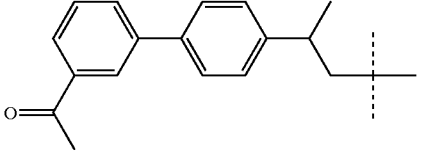 | Ex. 3 |
| 46 | 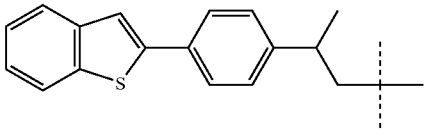 | Ex. 3 |
| 47 | 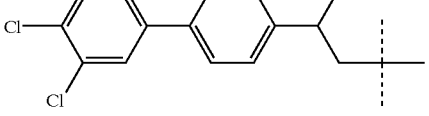 | Ex. 3 |
| 48 | 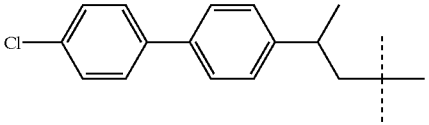 | Ex. 3 |
| 49 | 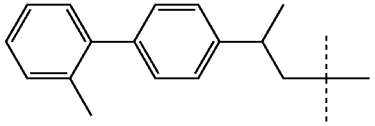 | Ex. 3 |
| 50 | 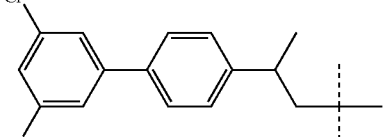 | Ex. 3 |
| 51 | 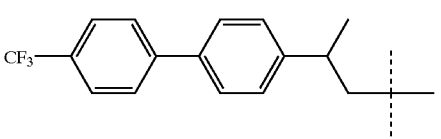 | Ex. 3 |

TABLE I-continued formula Ia

Q—N(H)—P(=O)(OEt)(OEt)

| Ex. | Q | S.M. |
|---|---|---|
| 52 | 3-nitro-biphenyl-4-yl-CH(CH₃)CH₂C(CH₃)₂– | Ex. 3 |
| 53 | PhC(=O)NH-CH₂CH₂-(biphenyl)-CH(CH₃)CH₂C(CH₃)₂– | Ex. 22 (amidation) |
| 54 | (CH₃)₂CHCH₂C(=O)NH-CH₂CH₂-(biphenyl)-CH(CH₃)CH₂C(CH₃)₂– | Ex. 22 (amidation) |
| 55 | 4-F-C₆H₄-C(=O)NH-CH₂CH₂-(biphenyl)-CH(CH₃)CH₂C(CH₃)₂– | Ex. 22 (amidation) |
| 56 | 3-MeO-C₆H₄-C(=O)NH-CH₂CH₂-(biphenyl)-CH(CH₃)CH₂C(CH₃)₂– | Ex. 22 (amidation) |
| 57 | 2-thienyl-C(=O)NH-CH₂CH₂-(biphenyl)-CH(CH₃)CH₂C(CH₃)₂– | Ex. 22 (amidation) |
| 58 | 2-MeO-C₆H₄-C(=O)NH-CH₂CH₂-(biphenyl)-CH(CH₃)CH₂C(CH₃)₂– | Ex. 22 (amidation) |
| 59 | PhCH₂C(=O)NH-CH₂CH₂-(biphenyl)-CH(CH₃)CH₂C(CH₃)₂– | Ex. 22 (amidation) |
| 60 | CH₃C(=O)NH-CH₂CH₂-(biphenyl)-CH(CH₃)CH₂C(CH₃)₂– | Ex. 22 (amidation) |

TABLE I-continued formula Ia

Q—N(H)—P(=O)(OEt)—OEt

| Ex. | Q | S.M. |
|---|---|---|
| 61 | benzyl-piperazinyl-phenyl-isobutyl group | Prep. 70 |
| 62 | methyl-piperazinyl-phenyl-isobutyl group | Prep. 70 |
| 63 | 2-fluorobiphenyl-ethyl group | Prep. 104 |

We claim:

1. A compound of the formula:

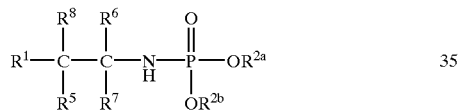

wherein

R$^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_yX^1R^9$ in which y is 0 or an integer of from 1 to 4, $X^1$ represents O, S, NR$^{10}$, CO, COO, OCO, CONR$^{11}$, NR$^{12}$CO, NR$^{12}$COCOO or OCONR$^{13}$, R$^9$ represents hydrogen, (1–10C)alkyl, (3–10C)alkenyl, (3–10C)alkynyl, pyrrolidinyl, tetrahydrofuryl, morpholino or (3–8C)cycloalkyl and R$^{10}$, R$^{11}$, R$^{12}$ and R$^{13}$ each independently represents hydrogen or (1–10C)alkyl, or R$^9$ and R$^{10}$, R$^{11}$, R$^{12}$ or R$^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula R$^{14}$—(L$^a$)$_n$—X$^2$—(L$^b$)$_m$ in which X$^2$ represents a bond, O, NH, S, SO, SO$_2$, CO, CH(OH), CONH, NHCO, NHCONH, NHCOO, COCONH, OCH$_2$CONH or CH=CH, L$^a$ and L$^b$ each represent (1–4C)alkylene, one of n and m is 0 or 1 and the other is 0, and R$^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, NR$^{16}$, CO, CH(OH), COO, OCO, CONR$^{17}$, NR$^{18}$CO, NHSO$_2$, NHSO$_2$NR$^{17}$, NHCONH, OCONR$^{19}$ or NR$^{19}$COO, R$^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N-(1–4C) alkoxycarbonyl)(1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and R$^{16}$, R$^{17}$, R$^{18}$ and R$^{19}$ each independently represents hydrogen or (1–10C)alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group; and R$^{2a}$ and R$^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

R$^8$ represents methyl and R$^5$, R$^6$, and R$^7$ represent hydrogen; or a pharmaceutically acceptable salt thereof.

2. A compound according to claim 1 which is diethyl N-2-(4-(3-thienyl)phenylpropyl)phosphoramidate and the pharmaceutically acceptable salts thereof.

3. A compound according to claim 1 which is diethyl N-2-(4-(2-fluorophenyl)phenylpropyl)phosphoramidate and the pharmaceutically acceptable salts thereof.

4. A pharmaceutical composition, which comprises a compound as claimed in claim 1 and a pharmaceutically acceptable diluent or carrier.

5. A method of potentiating glutamate receptor function in a mammal requiring such treatment, which comprises administering an effective amount of a compound of formula:

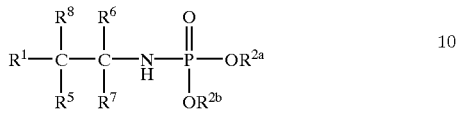

wherein
- $R^1$ represents an unsubstituted or substituted aromatic or heteroaromatic group;
- $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;
- $R^5$, $R^6 R^7$, and $R^8$ are each independently selected from the group consisting of hydrogen, (1–6C)alkyl; aryl (1–6C)alkyl; (2–6C)alkenyl; aryl(2–6C)alkenyl and aryl; or
- two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

6. A method of potentiating glutamate receptor function in a mammal requiring such treatment, which comprises administering an effective amount of a compound of the formula:

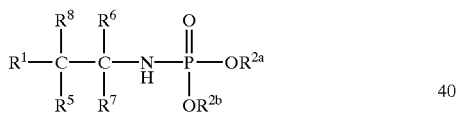

wherein
- $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}—(L^a)_n— X^2—(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2 NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N-(1–4C) alkoxycarbonyl)(1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and
- $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;
- $R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or
- two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

7. A method of treating a cognitive disorder; a neurodegenerative disorder; age-related dementia; age-induced memory impairment; movement disorder; reversal of a drug-induced state; depression; attention deficit disorder; attention deficit hyperactivity disorder; psychosis; cognitive deficits associated with psychosis; or drug-induced psychosis in a patient, which comprises administering to a patient in need thereof an effective amount of a compound of formula:

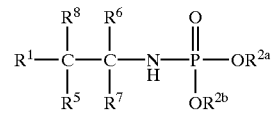

wherein
- $R^1$ represents an unsubstituted or substituted aromatic or heteroaromatic group;
- $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

8. A method of treating a cognitive disorder; a neurodegenerative disorder; age-related dementia; age-induced memory impairment; movement disorder; reversal of a drug-induced state; depression; attention deficit disorder; attention deficit hyperactivity disorder; psychosis; cognitive deficits associated with psychosis; or drug-induced psychosis in a patient, which comprises administering to a patient in need thereof an effective amount of a compound of the formula:

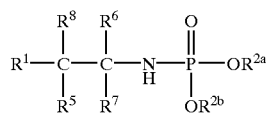

wherein $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C) alkylsulfonylamino(1–4C)alkyl, (N-(1–4C) alkoxycarbonyl)(1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

9. A method for improving memory or learning ability in a patient, which comprises administering to a patient in need thereof an effective amount of a compound of formula:

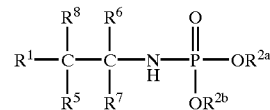

wherein $R^1$ represents an unsubstituted or substituted aromatic or heteroaromatic group;

$R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

10. A method for improving memory or learning ability in a patient, which comprises administering to a patient in need thereof an effective amount of a compound of the formula:

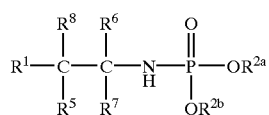

wherein $R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C)alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{2a}$ and $R^{2b}$ each independently represent hydrogen, (1–6C)alkyl, (3–6C)cycloalkyl, fluoro(1–6C)alkyl, chloro(1–6C)alkyl, (2–6C)alkenyl, (1–4C)alkoxy (1–4C)alkyl, phenyl which is unsubstituted or substituted by halogen, (1–4C)alkyl or (1–4C)alkoxy;

$R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

11. A compound according to claim 1 wherein $R^{2a}$ and $R^{2b}$ each independently represent (1–6C)alkyl.

12. A compound according to claim 11 wherein $R^{2a}$ and $R^{2b}$ each represent ethyl.

* * * * *